(12) United States Patent
Morino et al.

(10) Patent No.: US 11,445,903 B2
(45) Date of Patent: Sep. 20, 2022

(54) VISION TEST DEVICE

(71) Applicant: QD LASER, INC., Kawasaki (JP)

(72) Inventors: Seiji Morino, Kawasaki (JP); Makoto Suzuki, Kawasaki (JP); Mitsuru Sugawara, Kawasaki (JP); Kinya Hasegawa, Kawasaki (JP)

(73) Assignee: QD LASER, INC., Kawasaki (JP)

( * ) Notice: Subject to any disclaimer, the term of this patent is extended or adjusted under 35 U.S.C. 154(b) by 311 days.

(21) Appl. No.: 16/650,508

(22) PCT Filed: Aug. 23, 2018

(86) PCT No.: PCT/JP2018/031192
§ 371 (c)(1),
(2) Date: Mar. 25, 2020

(87) PCT Pub. No.: WO2019/069578
PCT Pub. Date: Apr. 11, 2019

(65) Prior Publication Data
US 2020/0275833 A1 Sep. 3, 2020

(30) Foreign Application Priority Data

Oct. 5, 2017 (JP) .............................. JP2017-195446

(51) Int. Cl.
*A61B 3/032* (2006.01)
*A61B 3/00* (2006.01)
(Continued)

(52) U.S. Cl.
CPC ............ *A61B 3/032* (2013.01); *A61B 3/0075* (2013.01); *A61B 3/0091* (2013.01); *A61B 3/024* (2013.01); *A61B 3/028* (2013.01); *A61B 3/036* (2013.01)

(58) Field of Classification Search
CPC ........ G02B 27/0172; G02B 2027/0178; A61B 3/028; A61B 3/12; A61B 3/032; A61B 3/1025; A61B 3/0285; A61B 3/0075
(Continued)

(56) References Cited

U.S. PATENT DOCUMENTS 6,008,781 A * 12/1999 Furness, III ....... G02B 27/0172
348/E9.026
7,637,615 B2 * 12/2009 Yamada ................. A61B 3/113
351/205
(Continued)

FOREIGN PATENT DOCUMENTS

JP         08-89480 A       4/1996
JP       2002-282299 A     10/2002
(Continued)

OTHER PUBLICATIONS

Yasuyuki Murai e t al., "Development of the fitting method of HMD (eyesight aid) to support visibility of low vision," Collection of papers of the 14th Forum on Information Technology, vol. 3, pp. 545-546, Aug. 24, 2015, with English translation.
(Continued)

*Primary Examiner* — Zachary W Wilkes
(74) *Attorney, Agent, or Firm* — Kenichiro Yoshida

(57) ABSTRACT

Provided is a vision test device including: a projection unit 10 that projects an image on a retina of a subject with use of a laser beam 50 by two-dimensionally scanning the laser beam; a beam diameter setting unit that sets a beam diameter of the laser beam; and a numerical aperture setting unit that sets a numerical aperture of the laser beam, wherein the projection unit projects, on the retina, a test image for measuring visual information of the subject with use of a laser beam having the set beam diameter and the set numerical aperture.

9 Claims, 20 Drawing Sheets

(51) Int. Cl.
*A61B 3/024* (2006.01)
*A61B 3/028* (2006.01)
*A61B 3/036* (2006.01)

(58) Field of Classification Search
USPC .......................................... 351/211, 222, 237
See application file for complete search history.

(56) References Cited

U.S. PATENT DOCUMENTS

| | | | | |
|---|---|---|---|---|
| 7,825,996 | B2* | 11/2010 | Yamada | G02B 27/017 |
| | | | | 348/744 |
| 7,891,812 | B2* | 2/2011 | Larichev | A61B 3/032 |
| | | | | 351/239 |
| 8,684,526 | B2* | 4/2014 | Neal | A61B 3/02 |
| | | | | 351/239 |
| 9,241,624 | B2* | 1/2016 | Cho | A61B 3/032 |
| 11,096,576 | B2* | 8/2021 | Dave | A61B 3/0008 |
| 2004/0109135 | A1* | 6/2004 | Watanabe | G09G 3/025 |
| | | | | 351/205 |
| 2009/0153796 | A1* | 6/2009 | Rabner | A61B 3/024 |
| | | | | 351/203 |
| 2014/0139404 | A1* | 5/2014 | Takeda | G02B 27/0172 |
| | | | | 345/8 |
| 2016/0089017 | A1 | 3/2016 | Wang | |
| 2017/0065161 | A1* | 3/2017 | Nozato | A61B 3/1015 |
| 2017/0068091 | A1* | 3/2017 | Greenberg | G06F 3/013 |
| 2018/0067326 | A1* | 3/2018 | Yon | G02B 17/08 |
| 2019/0353897 | A1* | 11/2019 | Suzuki | G02B 27/30 |
| 2020/0229694 | A1* | 7/2020 | Yasui | A61B 3/0091 |
| 2021/0173199 | A1* | 6/2021 | Suzuki | A61B 3/024 |

FOREIGN PATENT DOCUMENTS

| | | | | |
|---|---|---|---|---|
| JP | 2006-195084 | A | | 7/2006 |
| JP | 2012-053238 | A | | 3/2012 |
| JP | 2012053238 | A | * 3/2012 | ............. A61B 3/028 |
| JP | 2016-097194 | A | | 5/2016 |
| WO | 2014/167688 | A1 | | 10/2014 |
| WO | 2014/176070 | A1 | | 10/2014 |

OTHER PUBLICATIONS

Sachiko Udagawa et al., "How to Use Perimeter (Basic Operation): KO WA Automated Perimeter," Feature Article: The front line of perimetry, New Ophthalmology, vol. 31, No. 7, pp. 947-951, Jul. 31, 2014, with English Translation.

International Search Report for PCT/JP2018/031192 dated Nov. 20, 2018 with English Translation.

International Preliminary Report on Patentability dated Nov. 20, 2018 including a translation of Written Opinion of the International Searching Authority dated Apr. 16, 2020 for PCT/JP2018/031192.

* cited by examiner

VISION TEST DEVICE

TECHNICAL FIELD

The present invention relates to a vision test device, and relates to, for example, a vision test device for testing the vision of a subject.

BACKGROUND ART

It has been known to use an objective optometry device and a subjective optometry device for a test for vision, such as visual acuity, of a subject (for example, Patent Document 1).

PRIOR ART DOCUMENTS

Patent Document

Patent Document 1: Japanese Patent Application Publication No. H08-89480

SUMMARY OF THE INVENTION

Problem to be Solved by the Invention

The vision test includes measurements of the far visual acuity, the near visual acuity, the degree of astigmatism of a subject, and the diopter value of eye glasses suitable for the subject. Such vision tests are performed by adjusting the refractive index and the distortion of the lens. Therefore, the vision tests are conducted by an ophthalmologist or an optometrist, and takes time. Thus, the vision test cannot be conducted easily. In addition, it is difficult to measure the visual acuity of the retina that is not affected by the cornea, the crystalline lens, the vitreous body, and the like (hereinafter, referred to as an anterior eye part).

The present invention has been made in view of above problems, and aims to conduct a vision test of a subject appropriately.

Means for Solving the Problem

The present invention is a vision test device including: a projection unit that projects an image on a retina of a subject with use of a laser beam by two-dimensionally scanning the laser beam; a beam diameter setting unit that sets a beam diameter of the laser beam; and a numerical aperture setting unit that sets a numerical aperture of the laser beam, wherein the projection unit projects, on the retina, a test image for measuring visual information of the subject with use of a laser beam having the set beam diameter and the set numerical aperture.

In the above configuration, the projection unit can be configured to project, on the retina, an image for setting a numerical aperture suitable for the subject based on change in the numerical aperture.

In the above configuration, the numerical aperture setting unit can be configured to set the numerical aperture of the laser beam at the numerical aperture suitable for the subject, and the projection unit projects, on the retina, the test image for measuring the visual information of the subject with use of a laser beam having the numerical aperture suitable for the subject.

In the above configuration, the projection unit can be configured to project, on the retina, an image for calculating a diopter value of the subject based on change in the numerical aperture.

In the above configuration, the test image can be configured to be an image for measuring visual acuity or a visual field as the visual information of the subject or an image for assessing astigmatism.

In the above configuration, an input unit to which a response corresponding to visual recognition of the test image by the subject is input; and a control unit that measures the visual information of the subject based on a response input to the input unit may be provided.

In the above configuration, the control unit can be configured to determine a numerical aperture suitable for the subject based on a response of the subject input to the input unit in accordance with change in the numerical aperture, and measures the visual information of the subject based on a response input to the input unit in accordance with visual recognition of the test image projected on the retina with use of a laser beam having the numerical aperture suitable for the subject.

In the above configuration, the test image can be configured to contain test visual targets having different sizes for measuring the visual information of the subject.

In the above configuration, the test image can be configured to contain a fixation target for fixing a line of sight of the subject and a test visual target for measuring the visual information.

In the above configuration, the test image can be configured to contain a test visual target for measuring the visual information, and the test visual target blinks.

In the above configuration, an input unit to which information on a location within the retina on which a test visual target for measuring the visual information of the subject is to be projected may be provided, and the projection unit can be configured to project the test image on the retina such that the test visual target is projected on a location within the retina corresponding to the information on the location.

In the above configuration, the beam diameter setting unit can be configured to set a beam diameter of the laser beam at greater than 800 μm, and the projection unit projects, on the retina, the test image for measuring the visual information of the subject with use of a laser beam with a beam diameter greater than 800 μm.

In the above configuration, a revolving unit that revolves the laser beam emitted to an eyeball of the subject with respect to the eyeball; and an angle detection unit that detects an angle of the laser beam emitted to the eyeball to the eyeball of the projection unit may be provided.

Effects of the Invention

The present invention allows a vision test of a subject to be conducted appropriately.

EMBODIMENTS FOR CARRYING OUT THE INVENTION

Hereinafter, with reference to the accompanying drawings, embodiments of the present invention will be described.

First Embodiment

Figure 1:
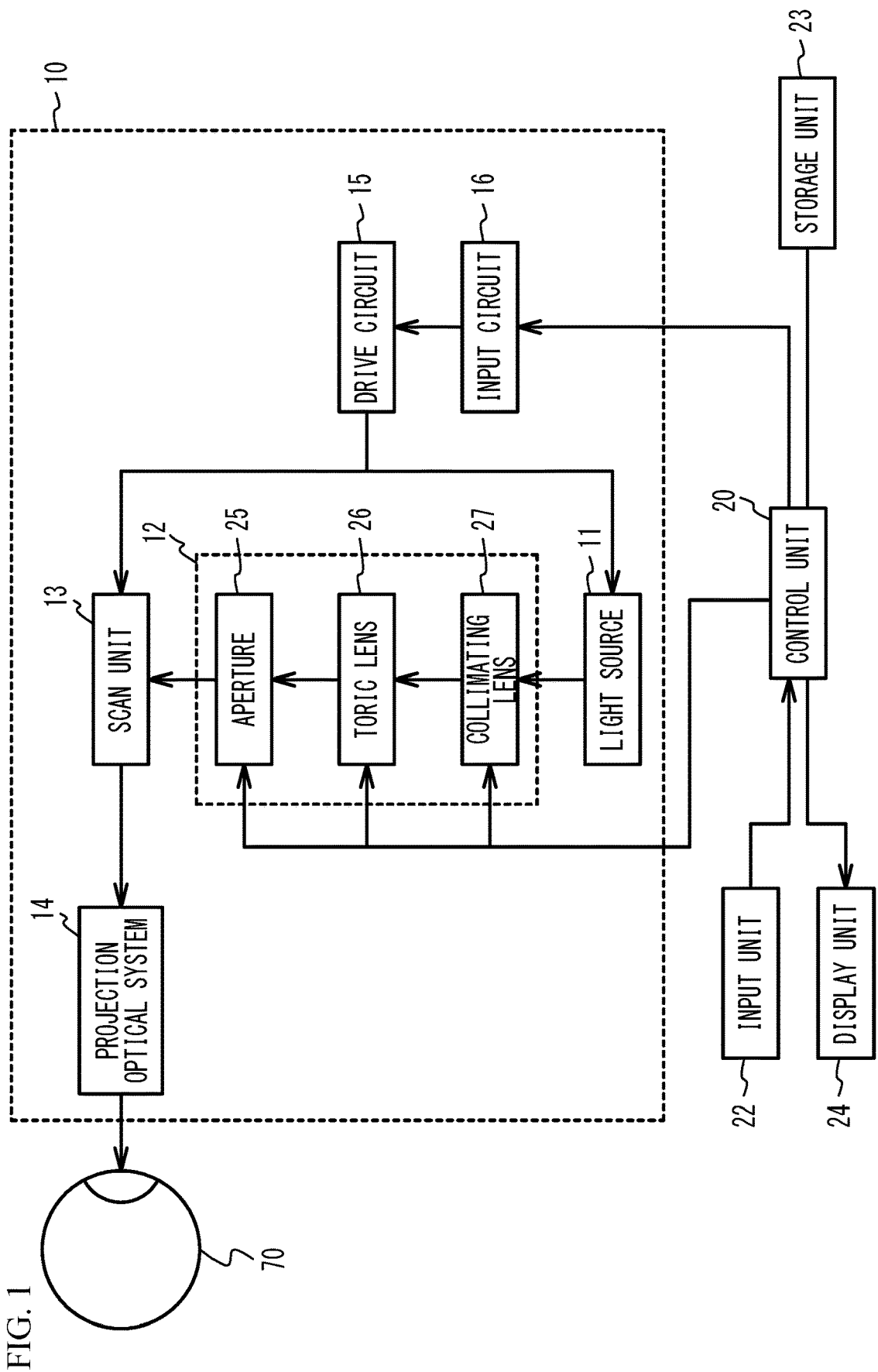
FIG. 1 is a block diagram of a vision test device in accordance with a first embodiment.

FIG. 1 is a block diagram of a vision test device in accordance with a first embodiment. As illustrated in FIG. 1, a projection unit 10, a control unit 20, an input unit 22, and a display unit 24 are provided. The projection unit 10 includes a light source 11, an adjustment unit 12, a scan unit 13, a projection optical system 14, a drive circuit 15, and an input circuit 16.

The control unit 20 generates an image to be projected on a retina. An image signal is input from the control unit 20 to the input circuit 16. The drive circuit 15 drives the light source 11 and the scan unit 13 according to an image signal obtained by the input circuit 16 and a control signal of the control unit 20.

The light source 11 emits, for example, a red laser beam (wavelength: approximately 610 nm to 660 nm), a green laser beam (wavelength: approximately 515 nm to 540 nm), and a blue laser beam (wavelength: approximately 440 nm to 480 nm). The light source 11 emitting red, green, and blue laser beams is, for example, a light source in which respective laser diode chips of RGB (red, green, blue), a device for synthesizing three colors, and a micro collimating lens are integrated. The light source 11 may be one light source, and may emit a laser beam of a single wavelength.

The adjustment unit 12 includes a collimating lens 27, a toric lens 26, an aperture 25, and the like, and shapes the laser beam 50. The scan unit 13 (a scanner) is, for example, a scan mirror such as a MEMS (Micro Electro Mechanical Systems) mirror or the like, or a transmission scanner, and scans the laser beam 50 in two-dimensional directions. The projection optical system 14 irradiates an eyeball 70 of a subject with the scanned laser beam 50.

In the control unit 20, a processor such as a CPU (Central Processing Unit) or the like may execute processes in cooperation with a program. The control unit 20 may be a specially designed circuit. The input unit 22 is a device to which the subject or an operator inputs results and the like, and is, for example, a button, a touch panel, a keyboard, and/or a mouse. The display unit 24 is, for example, a liquid crystal display or the like. A storage unit 23 is a volatile memory or a nonvolatile memory, and is, for example, a semiconductor memory or a hard disk drive.

Figure 2:
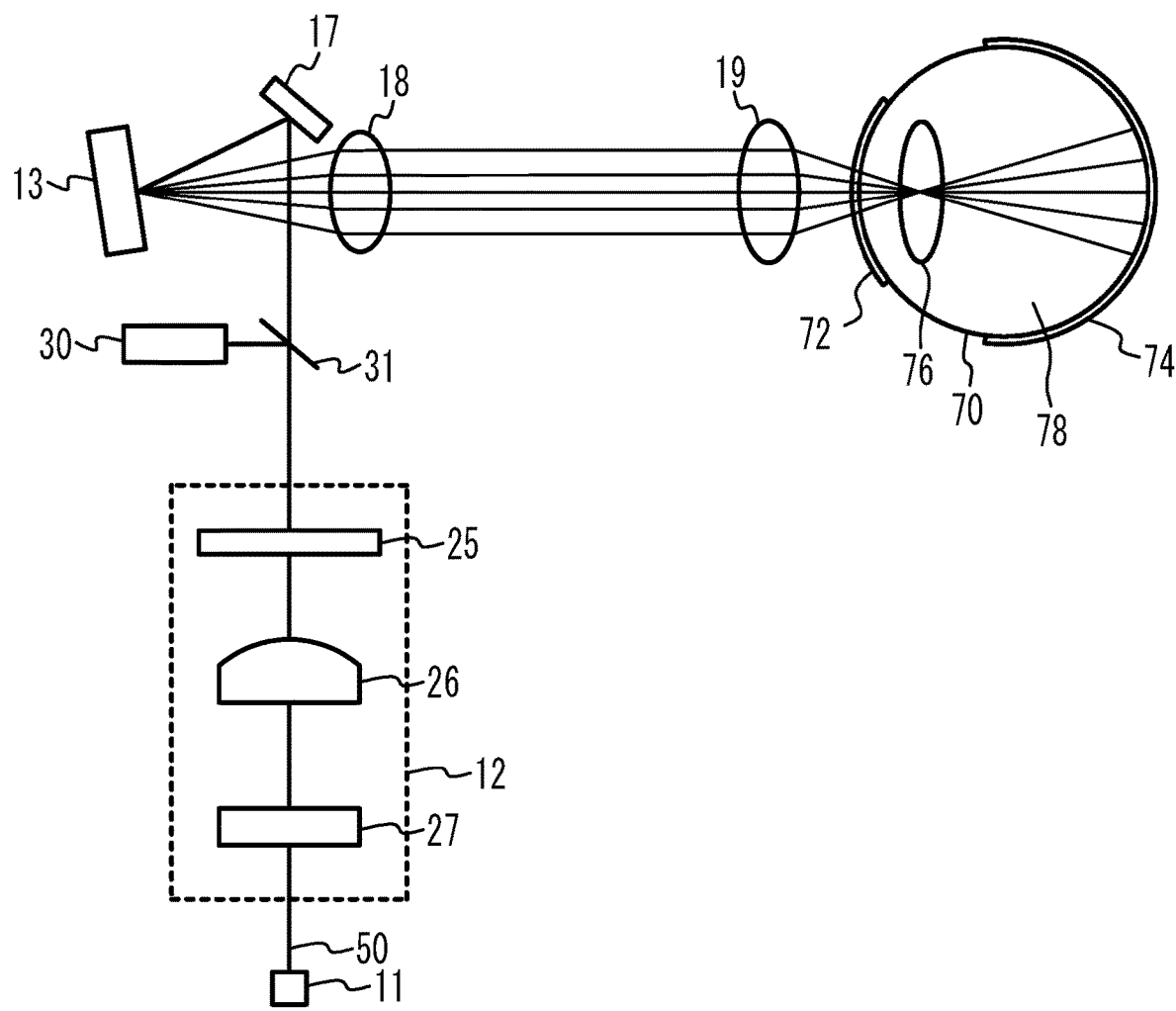
FIG. 2 illustrates an optical system of the vision test device of the first embodiment.

FIG. 2 illustrates an optical system of the vision test device in accordance with the first embodiment. The vision test device uses Maxwellian view to project a test image on the retina. The collimating lens 27 moves in the optical axis direction of the laser beam 50 to adjust the numerical aperture of the laser beam 50. The toric lens 26 causes the condensing power of the laser beam 50 to be different depending on the direction in the cross-section of the laser beam 50. The aperture 25 adjusts the diameter (hereinafter, referred to as a beam diameter) of the laser beam 50. A half mirror 31 reflects a part of the laser beam 50. A detector 30 detects the intensity of the reflected part of the laser beam 50. It is sufficient if the detector 30 and the half mirror 31 are located in any location of the path of the laser beam 50. The control unit 20 performs a feedback-control with output signals of the detector 30 such that the intensity of the laser beam 50 becomes a desired intensity.

The laser beam 50 reflected by the planar mirror 17 is two-dimensionally scanned by a MEMS mirror that is the scan unit 13. The scanned laser beam 50 is emitted to the eyeball 70 of the subject through the lenses 18 and 19. The laser beam 50 passes through a cornea 72, converges near a crystalline lens 76, passes through a vitreous body 78, and is emitted to a retina 74.

Figure 3:
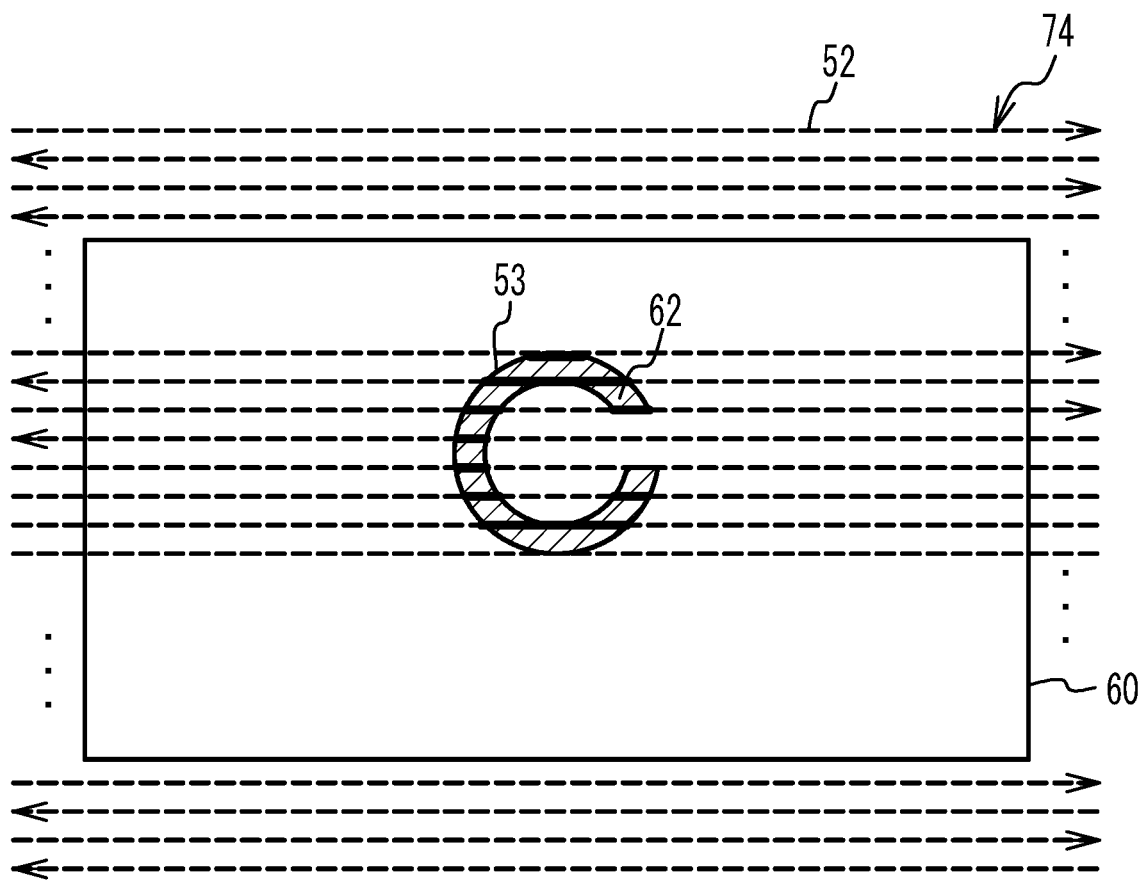
FIG. 3 illustrates a method of generating an image in the first embodiment.

FIG. 3 illustrates a method of generating an image in the first embodiment. As illustrated in FIG. 3, an image 60 is projected on the retina 74. The scan unit 13 raster-scans the laser beam 50 from the upper left to the lower right as indicated by arrows 52. Even though the scan unit 13 drives, when the light source 11 does not emit the laser beam 50, the retina 74 is not irradiated with the laser beam 50. The dashed line arrow 52 in FIG. 3 indicates that the laser beam 50 is not emitted. The drive circuit 15 synchronizes the light source 11 and the scan unit 13. Thereby, the light source 11 emits the laser beam 50 during the period indicated by a bold solid line 53. Thus, a Landolt ring or the like is projected, as a test visual target 62, on the retina 74, and no laser beam 50 is emitted to other regions. Hereinafter, the Landolt ring will be described as an example of the test visual target 62, but the test visual target 62 may be a character other than a Landolt ring.

[Experiment 1]

A typical visual acuity test, and a visual acuity test conducted by irradiating the retina 74 with the laser beam 50 as in the first embodiment were experimented. In the experiment, measured was how well subjects with different visual acuity of 0.04, 0.5, 0.9, and 1.2 in the typical visual acuity test could visually recognize the test visual target 62 projected on the retina 74 when the beam diameter of the laser beam 50 when entering the cornea 72 was varied. The image projected on the retina 74 was an image with a horizontal viewing angle of 20°, a screen aspect ratio of 16:9, and an effective vertical resolution of 720. For example, when the eye axial length is 24 mm, the dimensions of the image 60 projected on the retina 74 is 5700 μm×3200 μm in width and length.

Figure 4:
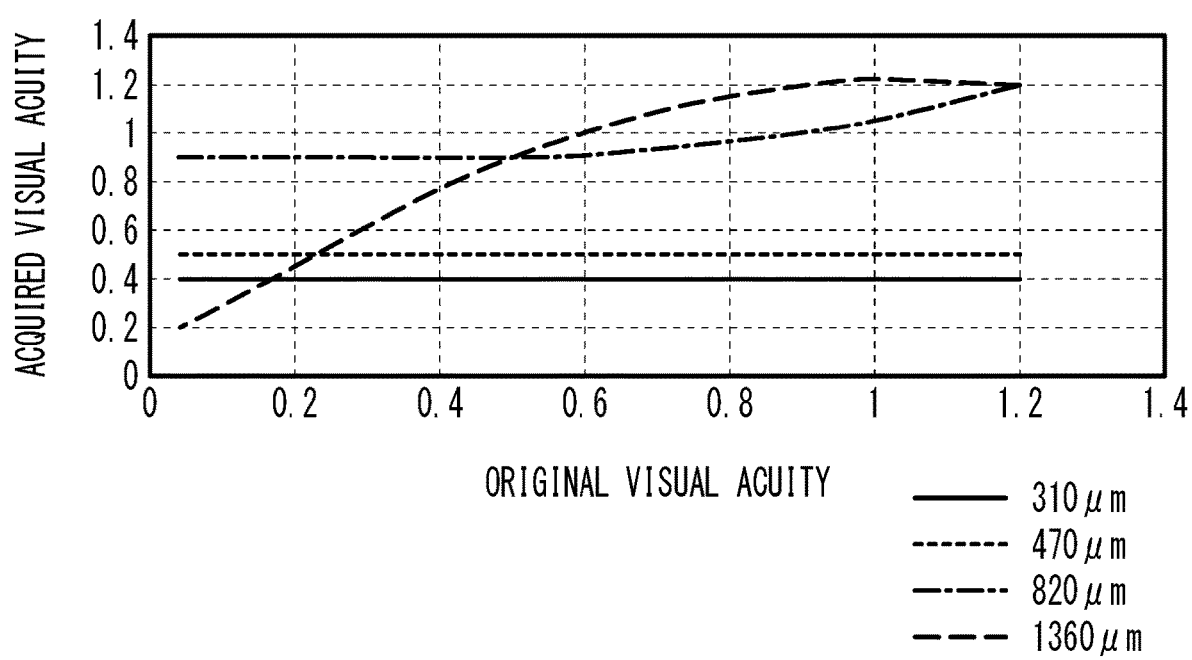
FIG. 4 presents results of an experiment 1.

FIG. 4 presents results of the experiment 1. In FIG. 4, the horizontal axis represents original visual acuity, and the vertical axis represents acquired visual acuity. The original visual acuity is defined as visual acuity measured by a typical visual acuity test. The acquired visual acuity is defined as visual acuity with respect to the test visual target 62 projected on the retina 74 of the subject, which is one of indicators of the visual acuity of the retina 74 that is not affected by the anterior eye part. The examined beam diameter of the laser beam 50 when entering the cornea 72 is 310 μm, 470 μm, 820 μm, and 1360 μm. The numerical aperture (NA) of the laser beam 50 when entering the cornea 72 is −0.001 to 0, and the laser beam 50 enters the cornea 72 as substantially parallel light. A negative numerical aperture indicates that the laser beam 50 enters the cornea 72 as convergent light.

As presented in FIG. 4, when the beam diameter of the laser beam 50 when entering the cornea 72 is 310 μm, the acquired visual acuity is substantially the same, approximately 0.4, even at different original visual acuity. When the beam diameter is 470 μm, the acquired visual acuity is substantially the same, approximately 0.5, even at different original visual acuity. On the other hand, when the beam diameter of the laser beam 50 when entering the cornea 72 is large, such as 820 μm and 1360 μm, as the original visual acuity changes, the acquired visual acuity also changes.

[Simulation 1]

Figure 5:
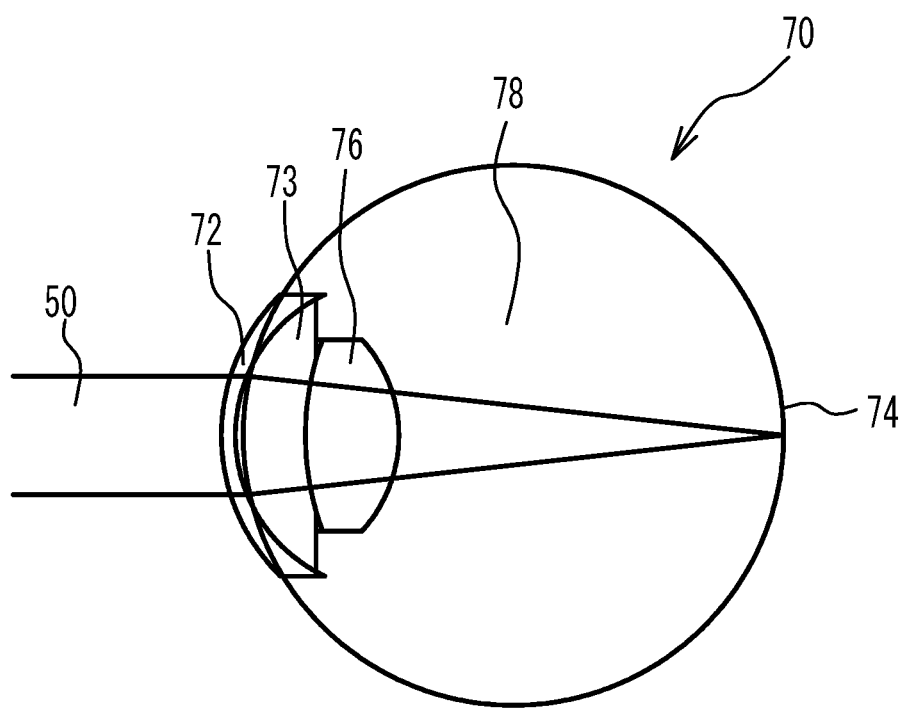
FIG. 5 illustrates an eyeball model used for a simulation.

FIG. 5 illustrates an eyeball model used for a simulation. As illustrated in FIG. 5, it was assumed that the eyeball 70 used for the simulation included the cornea 72, an anterior chamber 73, the crystalline lens 76, the vitreous body 78, and the retina 74, and the eye axial length was 24 mm. It was assumed that the laser beam 50 entered the cornea 72 as parallel light, passed through the cornea 72, the anterior chamber 73, the crystalline lens 76, and the vitreous body 78, and then was emitted to the retina 74. The refractive indexes of the cornea 72, the anterior chamber 73, the crystalline lens 76, and the vitreous body 78 were set at appropriate values.

In the simulation 1, the focal length was varied by changing the shape (the curvature) of the crystalline lens 76, thereby setting the original visual acuity. The acquired visual acuity was calculated using, as a reference, the actual measured value when the beam diameter of the laser beam 50 when entering the cornea 72 illustrated in FIG. 4 was 470 μm. That is, the beam diameter of the laser beam 50 on the retina 74 when the laser beam 50 with a beam diameter of 470 μm when entering the cornea 72 entered the eyeball 70 was calculated, and then, the ratio of the calculated beam diameter and the resolution necessary to obtain the acquired visual acuity when the beam diameter of the laser beam 50 in FIG. 4 was 470 μm was calculated. The acquired visual acuity when the beam diameter of the laser beam 50 on the retina 74 varied was calculated by varying the beam diameter of the laser beam 50 when entering the cornea 72 with use of the calculated ratio.

Figure 6:
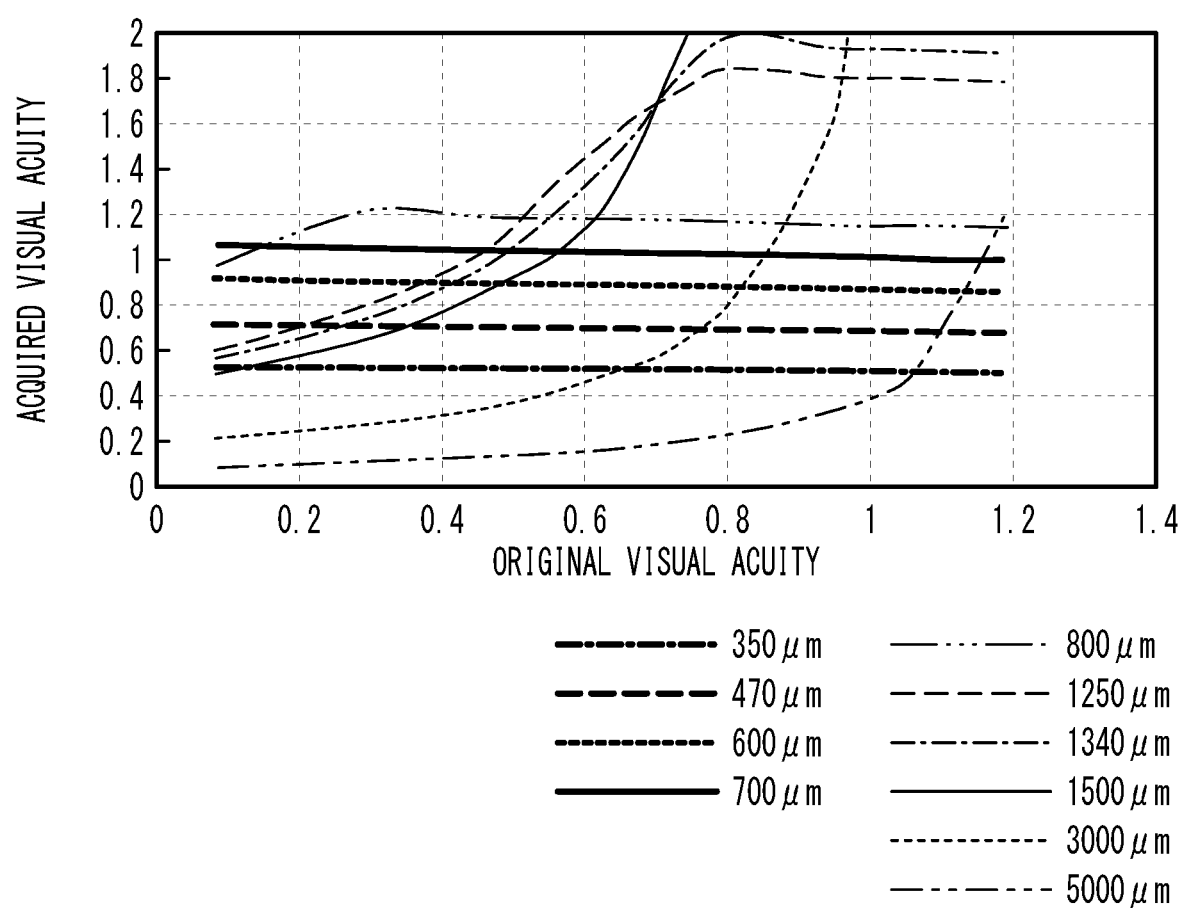
FIG. 6 presents results of a simulation 1.

FIG. 6 presents results of the simulation 1. In FIG. 6, the horizontal axis represents the original visual acuity, and the vertical axis represents the acquired visual acuity. The simulated beam diameter of the laser beam 50 when entering the cornea 72 is 350 μm, 470 μm, 600 μm, 700 μm, 800 μm, 1250 μm, 1340 μm, 1500 μm, 3000 μm, and 5000 μm.

As presented in FIG. 6, when the beam diameter of the laser beam 50 when entering the cornea 72 is 350 μm or greater and 800 μm or less, the acquired visual acuity is substantially the same even at different original visual acuity. The scanned laser beam 50 converges near the crystalline lens 76. Thus, the laser beam 50 with a small beam diameter is less likely to be affected by the lens function of the crystalline lens 76. This is considered the reason why the acquired visual acuity is substantially the same at different original visual acuity.

On the other hand, when the beam diameter of the laser beam 50 when entering the cornea 72 is greater than 800 μm, the acquired visual acuity depends on the original visual acuity. In particular, when the beam diameter of the laser beam 50 is 1250 μm or greater, the acquired visual acuity greatly depends on the original visual acuity. This is considered because the laser beam 50 with a large beam diameter is affected by the lens function of the crystalline lens 76.

[Simulation 2]

The relationship between the original visual acuity and the acquired visual acuity was simulated by varying the numerical aperture of the laser beam 50 when entering the cornea 72. The eyeball model described in FIG. 5 was used for a simulation 2. The original visual acuity and the acquired visual acuity were set and calculated by the respective methods described in the simulation 1.

Figure 7A:
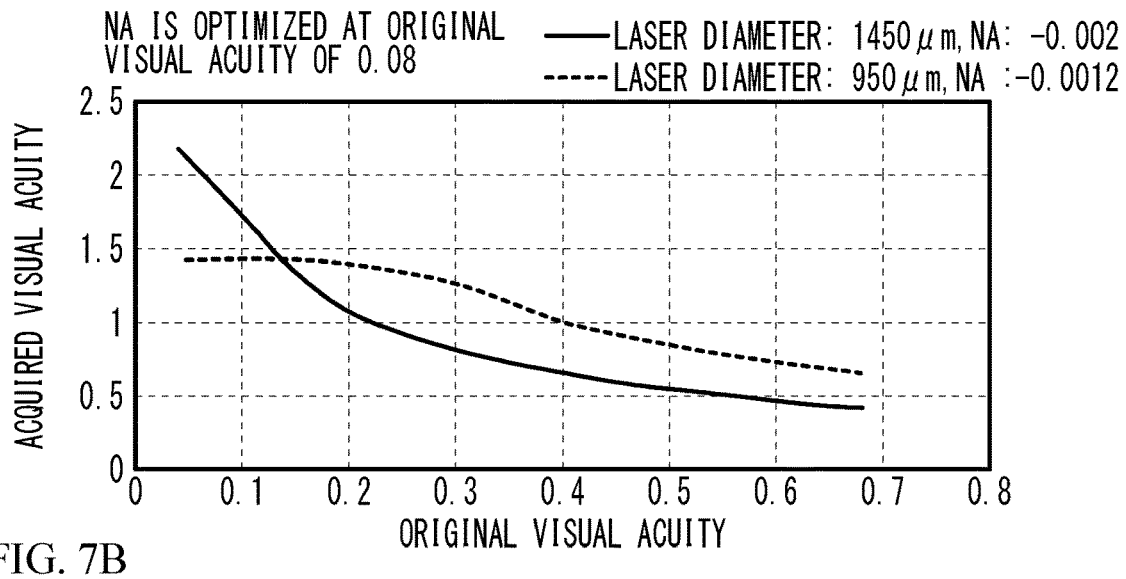
FIG. 7A to FIG. 7C present results of a simulation 2.
Figure 7B:
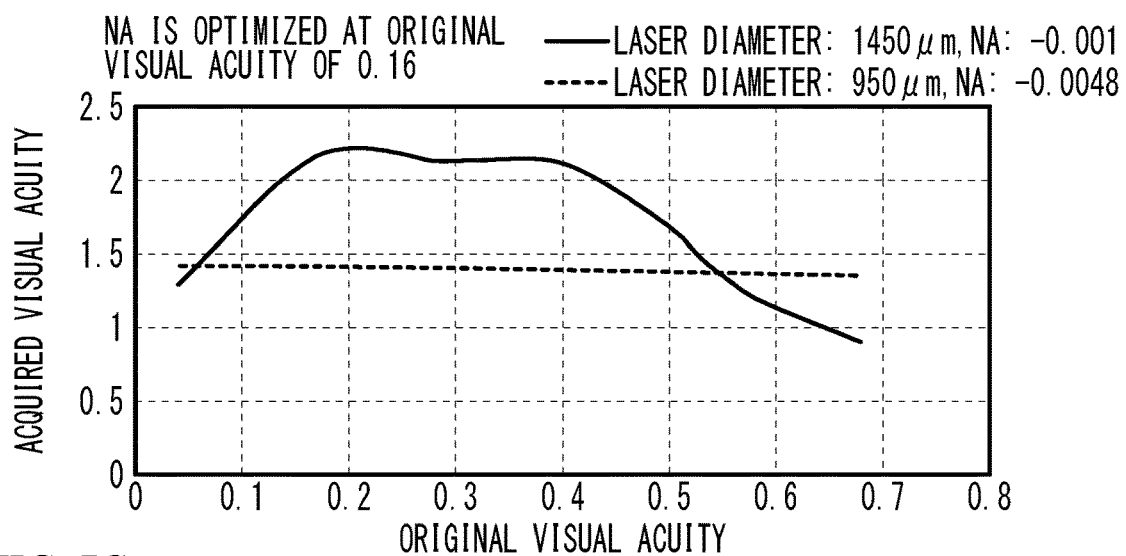
Figure 7C:
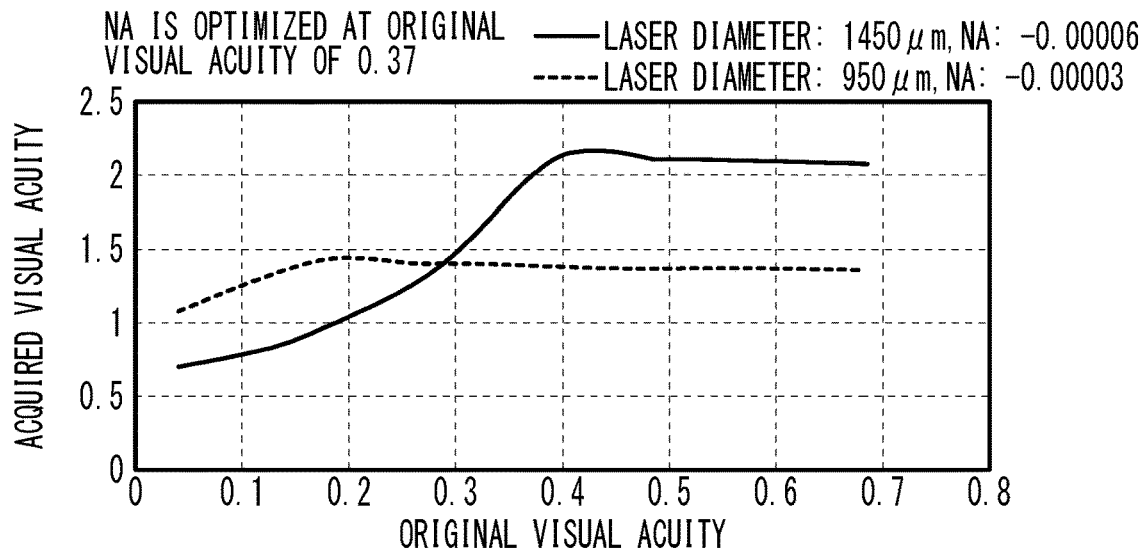

FIG. 7A to FIG. 7C present results of the simulation 2. FIG. 7A presents the simulation result when the numerical aperture was optimized at original visual acuity of 0.08. FIG. 7B presents the simulation result when the numerical aperture was optimized at original visual acuity of 0.16. FIG. 7C presents the simulation result when the numerical aperture was optimized at original visual acuity of 0.37. In FIG. 7A to FIG. 7C, the horizontal axis represents the original visual acuity, and the vertical axis represents the acquired visual acuity. The beam diameter of the laser beam 50 when entering the cornea 72 is 950 μm and 1450 μm.

As presented in FIG. 7A, at original visual acuity of 0.08, when the beam diameter of the laser beam 50 is 1450 μm, the optimum value of the numerical aperture is −0.002, and the acquired visual acuity is approximately 1.8. When the beam diameter of the laser beam 50 is 950 μm, the optimum value of the numerical aperture is −0.0012, and the acquired visual acuity is approximately 1.45.

As presented in FIG. 7B, at original visual acuity of 0.16, when the beam diameter of the laser beam 50 is 1450 μm, the optimum value of the numerical aperture is −0.001, and the acquired visual acuity is approximately 2.2. When the beam diameter of the laser beam 50 is 950 μm, the optimum value of the numerical aperture is −0.0048, and the acquired visual acuity is approximately 1.45.

As presented in FIG. 7C, at original visual acuity of 0.37, when the beam diameter of the laser beam 50 is 1450 μm, the optimum value of the numerical aperture is −0.00006, and the acquired visual acuity is approximately 2.2. When the beam diameter of the laser beam 50 is 950 μm, the optimum value of the numerical aperture is −0.00003, and the acquired visual acuity is approximately 1.45.

Based on the results of the experiment 1 and the simulation 1, when the beam diameter of the laser beam 50 is 800 μm or less, the laser beam 50 is less likely to be affected by the lens function of the crystalline lens 76, and when the beam diameter of the laser beam 50 is greater than 800 μm, the laser beam 50 is affected by the lens function of the crystalline lens 76. Based on the results of the simulation 2, when the beam diameter of the laser beam 50 is large, the acquired visual acuity can be increased by optimizing the numerical aperture. This is considered because optimization of the numerical aperture causes the laser beam 50 to be focused on the retina 74 when the beam diameter is large. In addition, since the beam diameter is large, the diameter of the laser beam 50 that is focused can be decreased. Thus, when the beam diameter is large, the acquired visual acuity can be increased.

In FIG. 6, when the beam diameter of the laser beam 50 is 800 µm, the acquired visual acuity is not the same with respect to the original visual acuity. This indicates that the lens function of the crystalline lens 76 affects the laser beam 50 when the beam diameter of the laser beam 50 is greater than 800 µm. When the beam diameter is 1250 µm, the acquired visual acuity greatly depends on the original visual acuity. This indicates that the lens function of the crystalline lens 76 greatly affects the laser beam 50 when the beam diameter is 1250 µm or greater. When the beam diameter is 5000 µm, the acquired visual acuity is less than the original visual acuity. Accordingly, the beam diameter is preferably 5000 µm or less, more preferably 3000 µm or less.

In the beam diameter with which the laser beam 50 is affected by the lens function of the crystalline lens 76, the numerical aperture suitable for the subject is measured. This allows the far visual acuity, the near visual acuity, the diopter value of eye glasses suitable for the subject, and the focal length of the subject to be determined. The acquired visual acuity is measured with the numerical aperture suitable for the subject. This allows the maximum acquired visual acuity to be measured. Furthermore, astigmatism can be examined by using the laser beam with a beam diameter with which the laser beam is affected by the lens function of the crystalline lens 76.

[Measurement of the Acquired Visual Acuity]

Figure 8:
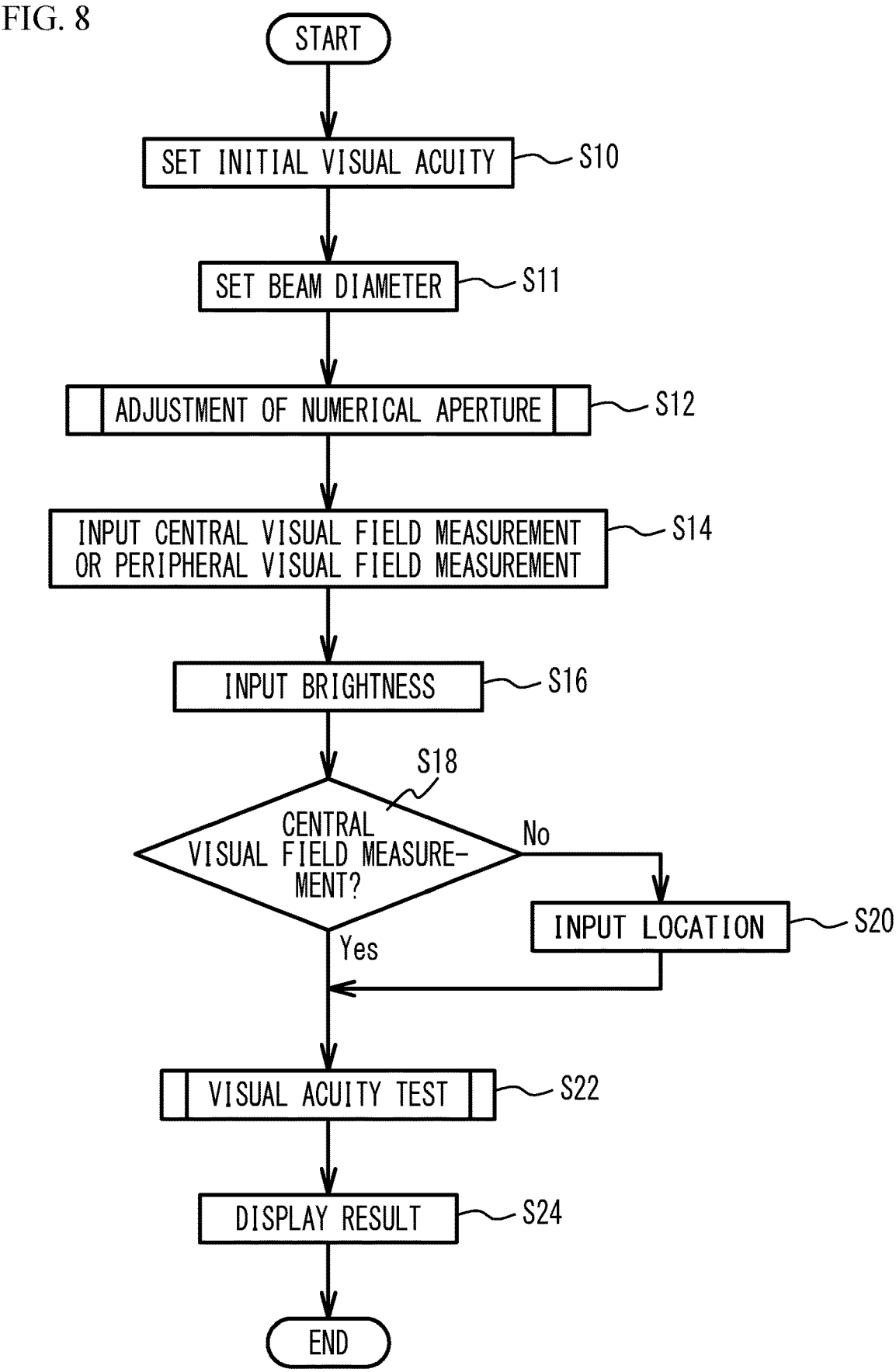
FIG. 8 is a flowchart of a method of measuring acquired visual acuity in the first embodiment.

FIG. 8 is a flowchart of a method of measuring the acquired visual acuity as visual information of the subject in the first embodiment. The control unit 20, the subject, or an examiner who conducts a test on the subject conducts each process. As illustrated in FIG. 8, initial visual acuity is set first (step S10).

Figure 9:
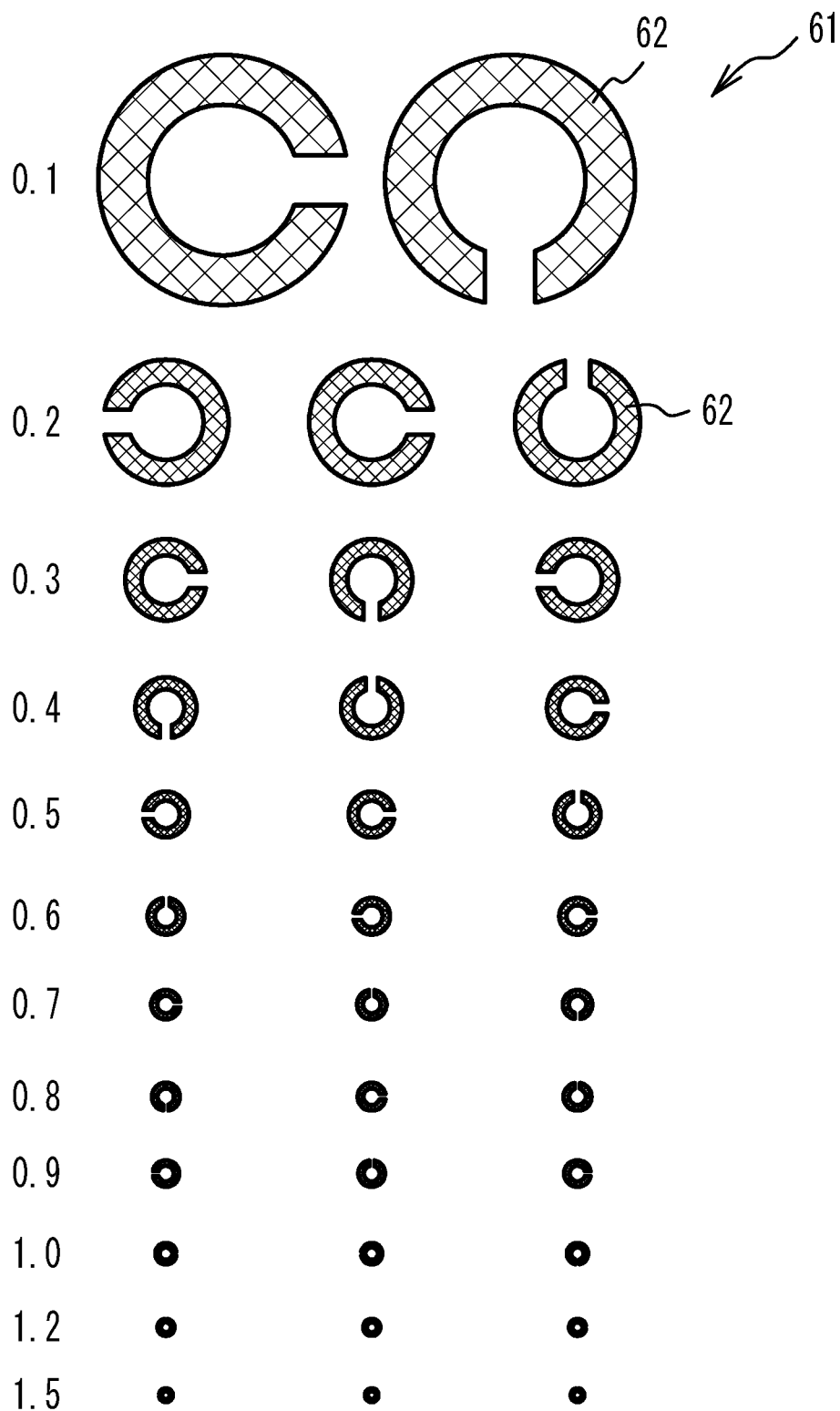
FIG. 9 illustrates an example of an image for initial setting in the first embodiment.

FIG. 9 illustrates an example of an image for initial setting in the first embodiment. As illustrated in FIG. 9, an initial setting image 61 contains a plurality of Landolt rings as a plurality of the test visual targets 62 corresponding to the visual acuity of 0.1 to 1.5. The projection unit 10 projects the initial setting image 61 on the retina 74. The subject or the examiner inputs, as the initial visual acuity, the value (corresponding to the visual acuity) of the smallest test visual target 62 that the subject can visually recognize, through the input unit 22. The setting of the initial visual acuity may be obtained by the control unit 20 from the storage unit 23.

Back to FIG. 8, the size of the beam diameter of the laser beam 50 is set (step S11). For example, the beam diameter of the laser beam 50 when entering the cornea 72 is set at greater than 800 µm with use of the aperture 25. The control unit 20 or the examiner who conducts a test on the subject sets the beam diameter. The aperture 25 may be fixed, and the beam diameter may be fixed to a value greater than, for example, 800 µm.

The aperture 25 may be, for example, a disk-shaped plate. A plurality of holes with different diameters are arranged in a concentric pattern in the disk-shaped plate. The hole with a desired diameter is selected by revolving the disk-shaped plate around the center of the concentric circle. When the laser beam 50 passes through the selected hole, the beam diameter of the laser beam 50 is set. The aperture 25 may be, for example, a plate including a hole having a diaphragm mechanism. The beam diameter of the laser beam 50 passing through the hole is set by varying the diameter of the hole by the diaphragm mechanism.

The numerical aperture is adjusted (step S12). The numerical aperture is adjusted by projecting the test visual target 62 corresponding to the initial visual acuity on the retina 74. Selection of central visual field measurement or peripheral visual field measurement is input in accordance with the condition of the visual field of the subject and the measurement purpose (step S14). The selection of the central visual field measurement or the peripheral visual field measurement may be input through the input unit 22 by the subject or the examiner, or may be obtained by the control unit 20 from the storage unit 23.

Figure 10A:
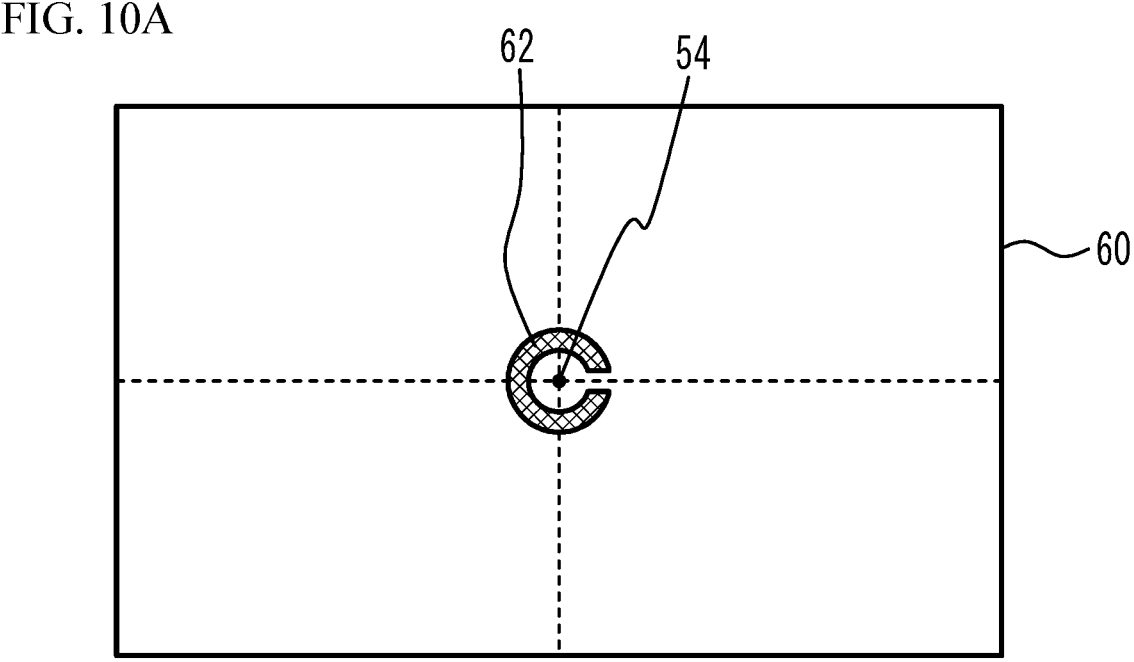
FIG. 10A and FIG. 10B illustrate an example of projection of a test image on a central visual field or a peripheral visual field in the first embodiment.
Figure 10B:
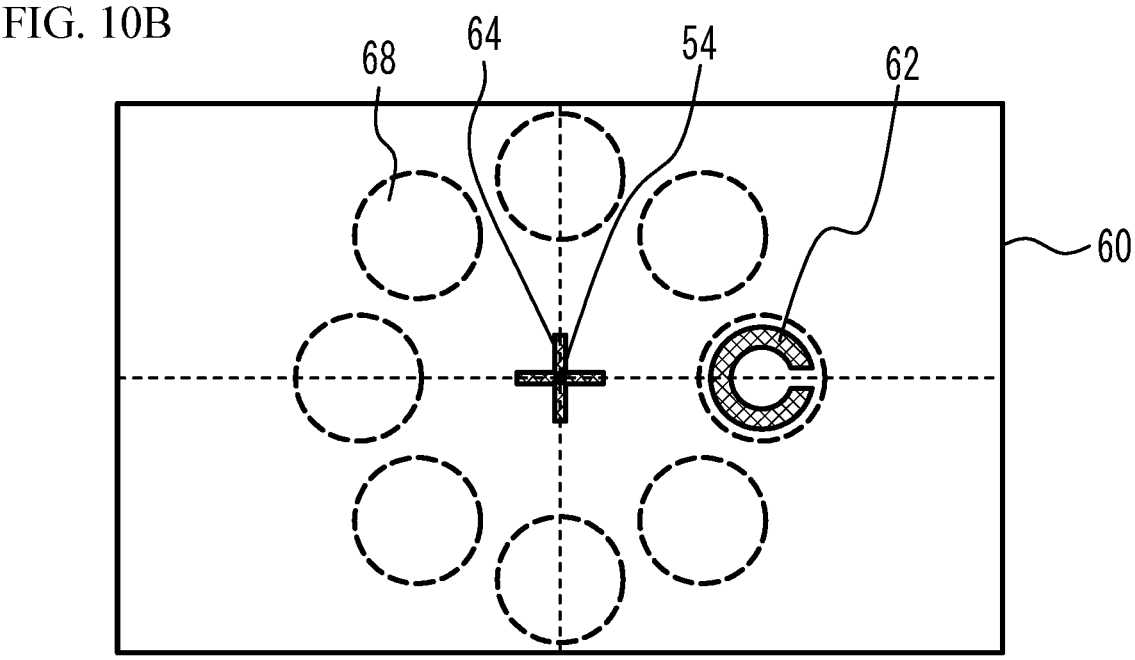

FIG. 10A and FIG. 10B illustrate examples of the projection of the test visual target on the central visual field or the peripheral visual field in the first embodiment. FIG. 10A and FIG. 10B illustrate the image 60 to be projected on the retina 74. A center 54 of the image 60 is projected on the center of the retina 74. As illustrated in FIG. 10A, for the measurement of the central visual field, the test visual target 62 such as a Landolt ring or the like is projected near the center of the retina 74. As illustrated in FIG. 10B, for the measurement of the visual acuity in the peripheral visual field, a fixation target 64 for fixing the line of sight of the subject is projected on the center 54 of the image. The test visual target 62 such as a Landolt ring or the like is projected on a region 68 around the fixation target 64.

Back to FIG. 8, the brightness is input (step S16). The brightness is the brightness of the test visual target 62. For example, since the periphery of the retina 74 has a lower sensitivity than the center of the retina 74, the brightness in the measurement of the peripheral visual field is set at higher than that in the measurement of the central visual field. The brightness may be input by the subject or the examiner through the input unit 22, may be obtained by the control unit 20 from the storage unit 23, or may be determined by the control unit 20. The contrast of the image may be set in addition to the brightness. To make the brightness constant, the control unit 20 may feedback-control the intensity of the laser beam 50 with use of an output signal of the detector 30.

The brightness of the test visual target 62 can be set by controlling the output of the light source 11. Alternatively, a mechanism allowing a neutral density filter to be selected may be provided in the light path of the laser beam 50. The brightness of the test visual target 62 can be set by selecting the neutral density filter that allows the laser beam 50 to pass therethrough.

The control unit 20 determines whether the measurement selected in step S14 is the central visual field measurement (step S18). When the determination is Yes, the process proceeds to step S22. When the determination is No, the location where the peripheral visual field is to be measured is input (step S20). The location where the peripheral visual field is to be measured can be selected from, for example, eight locations such as the regions 68 in FIG. 10B. The distance, from the center 54, of the location where the peripheral visual field is to be measured may be input. The location where the peripheral visual field is to be measured may be input by the subject or the examiner through the input unit 22, may be obtained by the control unit 20 from the storage unit 23, or may be determined by the control unit 20. The visual acuity test is conducted (step S22). The control unit 20 displays the result of the visual acuity test on the display unit 24 (step S24).

Figure 11:
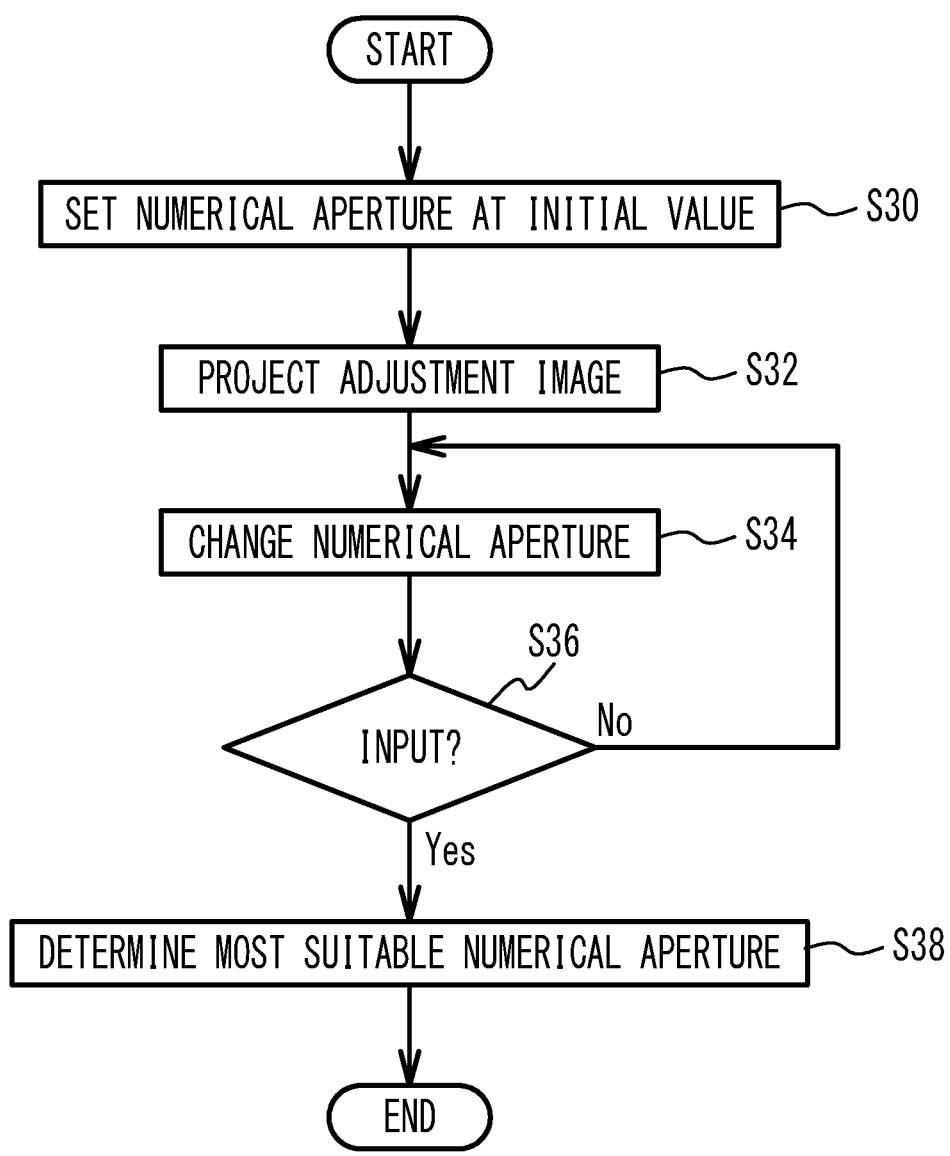
FIG. 11 is a flowchart of a method of adjusting a numerical aperture in the first embodiment.

FIG. 11 is a flowchart of a method of adjusting the numerical aperture (step S12 in FIG. 8) in the first embodiment. As illustrated in FIG. 11, the numerical aperture is set at an initial value (step S30). The numerical aperture is adjusted by, for example, moving the collimating lens 27 in the optical axis direction. The numerical aperture may be set at the initial value by the subject or the examiner through the input unit 22, or may be set by the control unit 20. In the case of a general-purpose measurement, the initial value stored in advance in the storage unit 23 or the like may be used as the initial value of the numerical aperture. In addition, the initial value of the numerical aperture may be selected in accordance with the condition of the subject, such as the initial value for myopia or the initial value for hyperopia.

The control unit 20 generates an adjustment image, and causes the projection unit 10 to project the generated adjustment image on the retina 74 (step S32). For example, the projection unit 10 projects, on the retina 74, the adjustment image such as a Landolt ring or the like corresponding to the initial visual acuity set in step S10 of FIG. 8 in accordance with the instruction from the control unit 20 or the examiner.

Figure 12A:
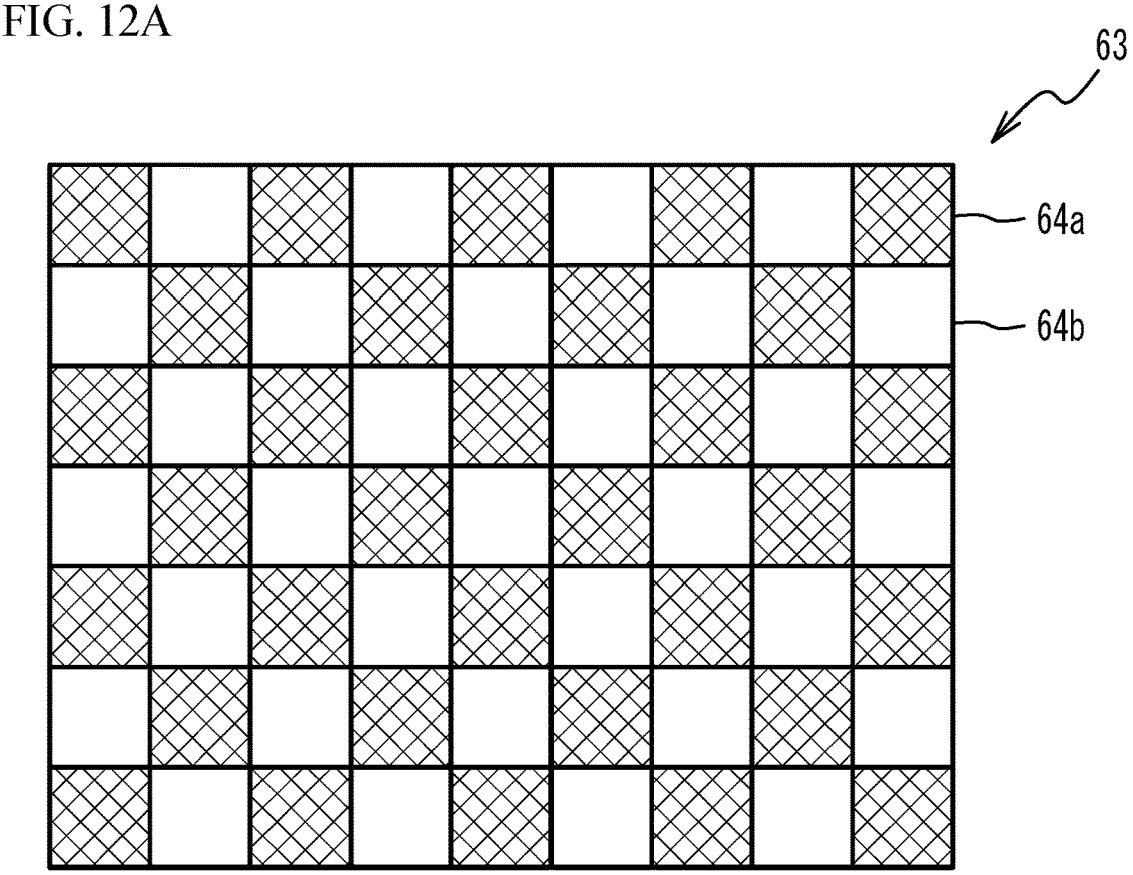
FIG. 12A and FIG. 12B illustrate another example of an adjustment image in the first embodiment.
Figure 12B:
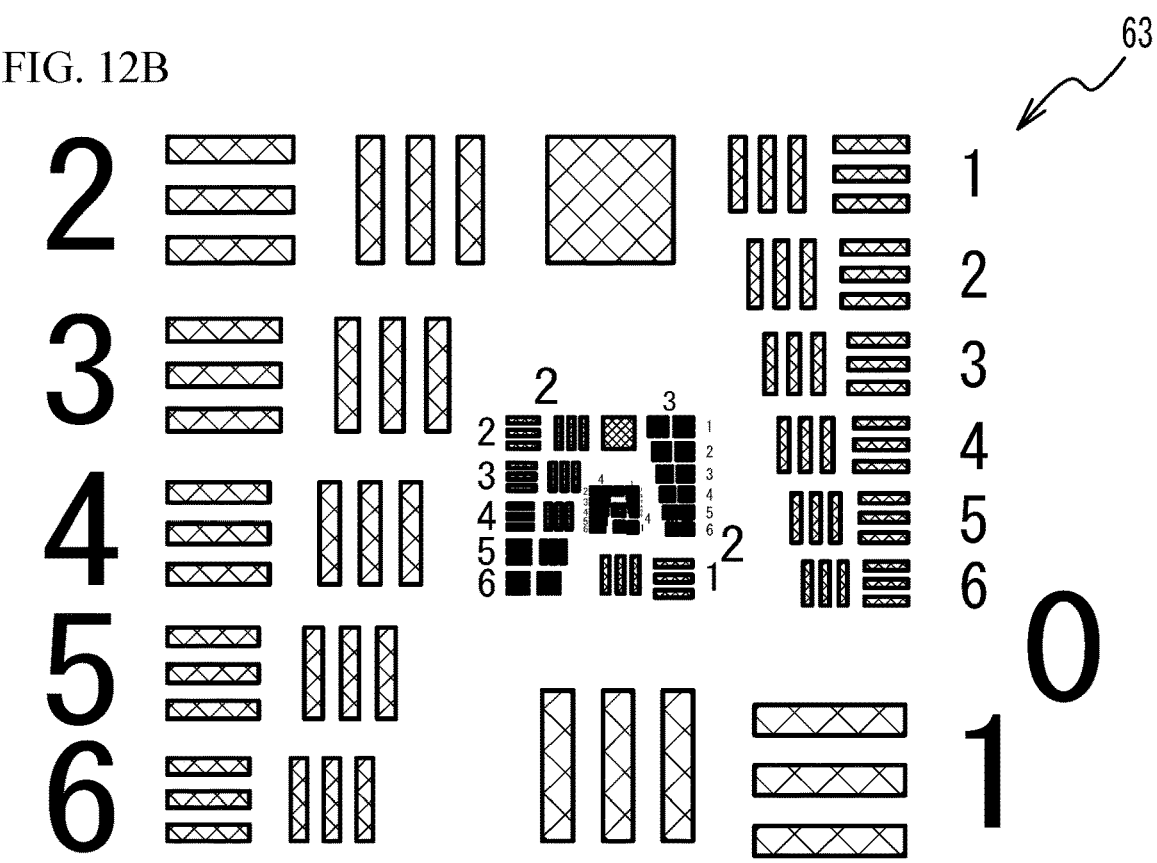

FIG. 12A and FIG. 12B illustrate other examples of the adjustment image in the first embodiment. As illustrated in FIG. 12A, an adjustment image 63 may be a checkered pattern having dark sections 64a and bright sections 64b. The size of each of the dark section 64a and the bright section 64b is, for example, 1°, 0.5°, or 0.25° in viewing angle. As illustrated in FIG. 12B, the adjustment image 63 may be a resolution chart.

Back to FIG. 11, the numerical aperture is changed (step S34). For example, the numerical aperture is changed from the initial value of the numerical aperture. The control unit 20 or the examiner changes the numerical aperture by moving the collimating lens 27. It is determined whether the determination is input (step S36). For example, the control unit 20 or the examiner continuously changes the numerical aperture, and the subject operates the input unit 22 at a timing when the subject can visually recognize the adjustment image 63 best.

When the determination is No in step S36, the process returns to step S34, and changing of the numerical aperture is continued. When the determination is Yes, the numerical aperture most suitable for the subject is determined (step S38). For example, the numerical aperture when the determination is input in step S36 is determined as the numerical aperture most suitable for the subject. Thereafter, the process is ended, and returns to FIG. 8.

The method of setting the numerical aperture is not limited to the method that moves the collimating lens 27. For example, the numerical aperture setting unit may include relay lenses with different focal lengths, and change the numerical aperture by changing the combination of these relay lenses. The numerical aperture setting unit may have an aperture for setting the numerical aperture, and change the numerical aperture by changing the diameter of the aperture. That is, the numerical aperture can be changed by varying the focal length of the laser beam and the diameter of the aperture.

In addition, as the method of adjusting the numerical aperture, the numerical aperture may be adjusted such that the subject can visually recognize the adjustment image 63 best as in the first embodiment. Alternatively, the values of the numerical aperture corresponding to myopia, hyperopia, astigmatism, or an ophthalmologic disease may be stored in advance in the storage unit 23 or the like, and the control unit 20 or the examiner may set the numerical aperture at the stored value of the numerical aperture.

Figure 13:
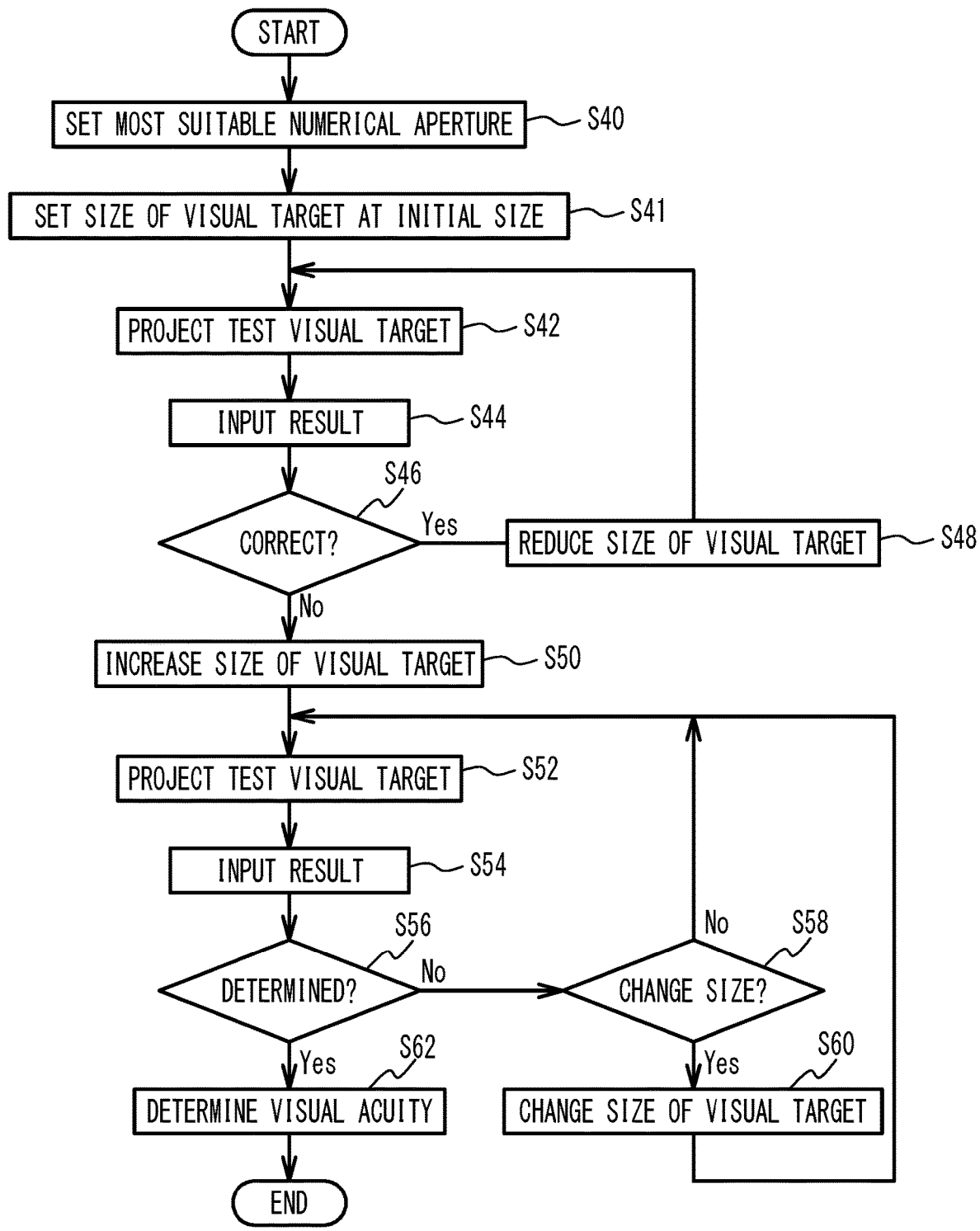
FIG. 13 is a flowchart of a method of a visual acuity test in the first embodiment.

FIG. 13 is a flowchart of a method of the visual acuity test (step S22 in FIG. 8) in the first embodiment. As illustrated in FIG. 13, the numerical aperture is set at the most suitable numerical aperture determined in step S38 of FIG. 11 (step S40). For example, the control unit 20 or the examiner sets the numerical aperture at the most suitable numerical aperture with use of the collimating lens 27. The size of the test visual target 62 is set at an initial size (step S41). For example, the size of the test visual target 62 such as a Landolt ring or the like is set at the size corresponding to the initial visual acuity set in step S10 of FIG. 8. The initial size may be set by the subject or the examiner through the input unit 22, or may be set by the control unit 20.

The vision test device may include a positional information detection unit that can detect the position of the collimating lens 27. The positional information detection unit measures the position of the collimating lens 27. This structure allows the control unit 20 to obtain the position of the collimating lens 27, and control the numerical aperture in accordance with the position of the collimating lens 27.

The test visual target 62 having the size that has been set is projected on the retina (step S42). For example, the control unit 20 or the examiner causes the projection unit 10 to project, on the retina 74, the test visual target 62 with the size that has been set. In this case, the location on which the test visual target 62 is to be projected within the retina 74 is the location input in steps S14 and S20 of FIG. 8. In addition, the brightness of the test visual target 62 is the brightness input in step S16 of FIG. 8.

The result is input (step S44). For example, when the subject can visually recognize the direction of a Landolt ring, which is the test visual target 62, the subject or the examiner input the visually-recognized direction to the input unit 22. The control unit 20 or the examiner determines whether the input result is correct (step S46). For example, the control unit 20 determines whether the input direction of the Landolt ring is correct. When the determination is Yes, the size of the test visual target 62 is reduced (step S48). For example, the control unit 20 or the examiner reduces the size of the test visual target 62 by one rank. The process returns to step S42.

When the determination is No in step S46 as the result of visual recognition by the subject, the size of the test visual target 62 is increased (step S50). For example, the control unit 20 or the examiner increases the size of the test visual target 62 by one rank. As in step S42, the test visual target 62 is projected on the retina 74 (step S52). As in step S44, the result is input (step S54).

It is determined whether the visual acuity can be determined (step S56). For example, the control unit 20 or the examiner determines whether the visual acuity of the subject can be determined from the test results so far. When the determination is No, it is determined whether the size of the test visual target 62 is to be changed (step S58). For example, the control unit 20 or the examiner determines whether to change the size of the test visual target 62, from the test results so far. When the determination is No, the process returns to step S52.

When the determination is Yes, the size of the test visual target 62 is changed (step S60). For example, the control unit 20 or the examiner changes the size of the test visual target 62. The process returns to step S52. When the determination is Yes as a result of the visual recognition by the subject in step S56, the visual acuity of the subject is determined (step S62). For example, the control unit 20 or the examiner determines the visual acuity of the subject. Thereafter, the process returns to FIG. 8.

Examples of the processes in steps S56 and S58 will be described. The processes from the steps S52 to S60 are repeated up to five times with the test visual targets 62 having the same size. When the answer is correct three times with respect to the test visual targets 62 having the same size, the size of the test visual target 62 is reduced by one rank, and the process returns to step S52. When the answer is incorrect three times with respect to the test visual targets 62 having the same size, the visual acuity corresponding to the smallest test visual targets 62 with respect to which the answer was correct three times. When the answer is incorrect three times in the first five times, the size of the test visual target 62 is increased by one rank, and the process returns to step S52.

Figure 14A:
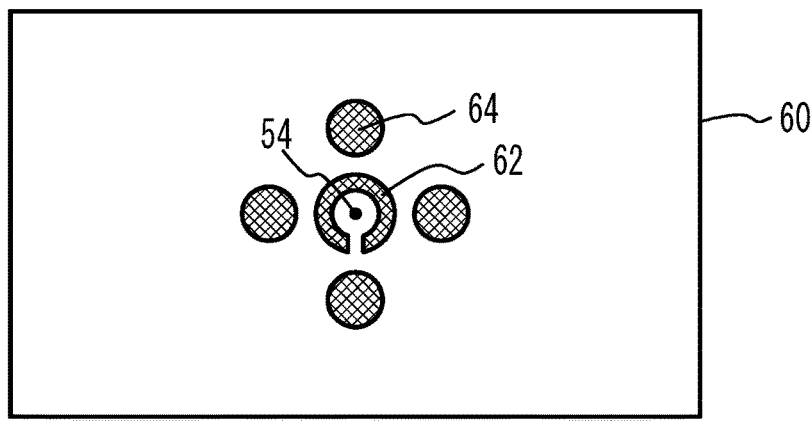
FIG. 14A to FIG. 14D illustrate examples of an image in the first embodiment.

FIG. 14A to FIG. 14D illustrate examples of the image in the first embodiment. As illustrated in FIG. 14A, in the image 60 for measuring the acquired visual acuity of the central visual field, a Landolt ring is projected as the test visual target 62 at the center of the image 60. A plurality of dot patterns is projected as the fixation targets 64 so as to surround the test visual target 62. When the subject uniformly sees the plurality of dot patterns, the test visual target 62 is projected at the center of the retina 74.

Figure 14B:
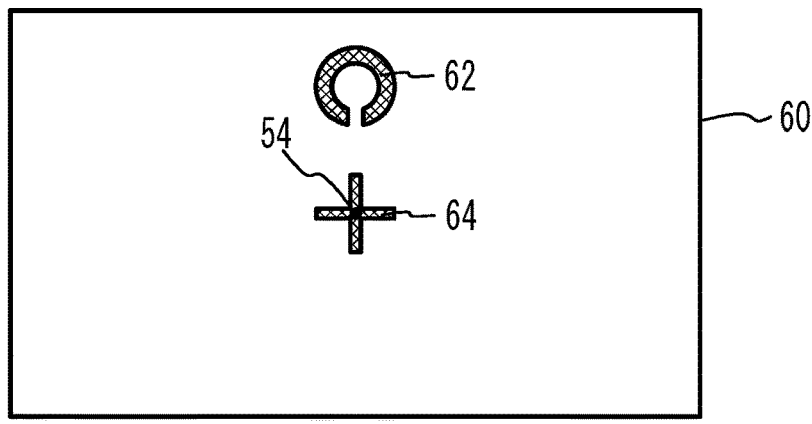
Figure 14C:
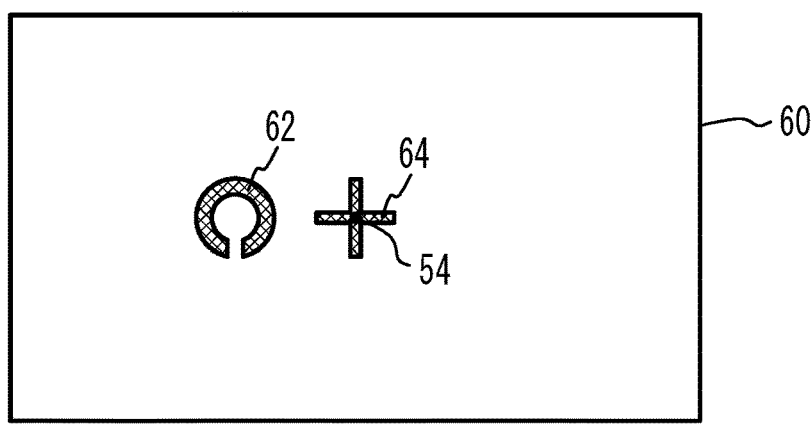
Figure 14D:
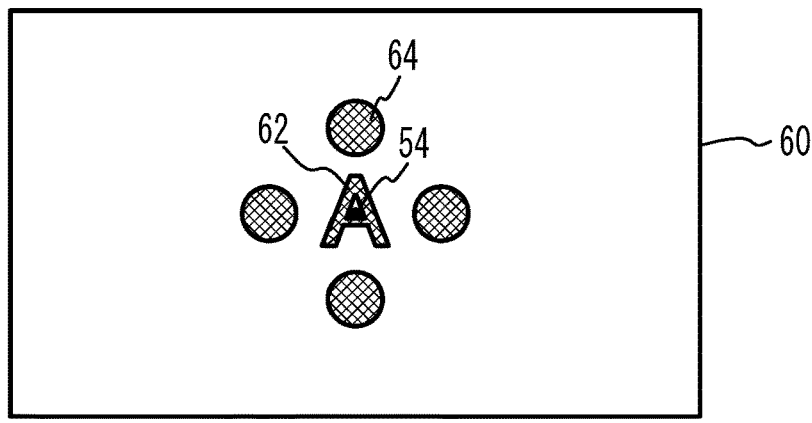

An example where the image 60 to be projected on the retina 74 has a fixation target will be described. As illustrated in FIG. 14B and FIG. 14C, in the image 60 for measuring the acquired visual acuity of the peripheral visual field, the fixation target 64 is projected at the center 54 of the image 60. The test visual target 62 is projected on a desired location within the retina 74 by making the subject fix the eye of the subject on the fixation target 64. As illustrated in FIG. 14D, the test visual target 62 may be a character.

When the test visual target 62 is projected near the retina 74 without projecting the fixation target 64 near the center of the retina 74, the line of sight of the subject moves to the fixation target 64. By projecting the fixation target 64 at the center 54 of the image 60, the vicinity of the center 54 of the image 60 is projected near the center of the retina 74. To fix the line of sight of the subject, the test visual target 62 may be made to blink without displaying the fixation target 64. This inhibits the line of sight of the subject from moving to the test visual target 62. Thus, the test visual target 62 can be projected on the desired region of the retina 74.

Figure 15:
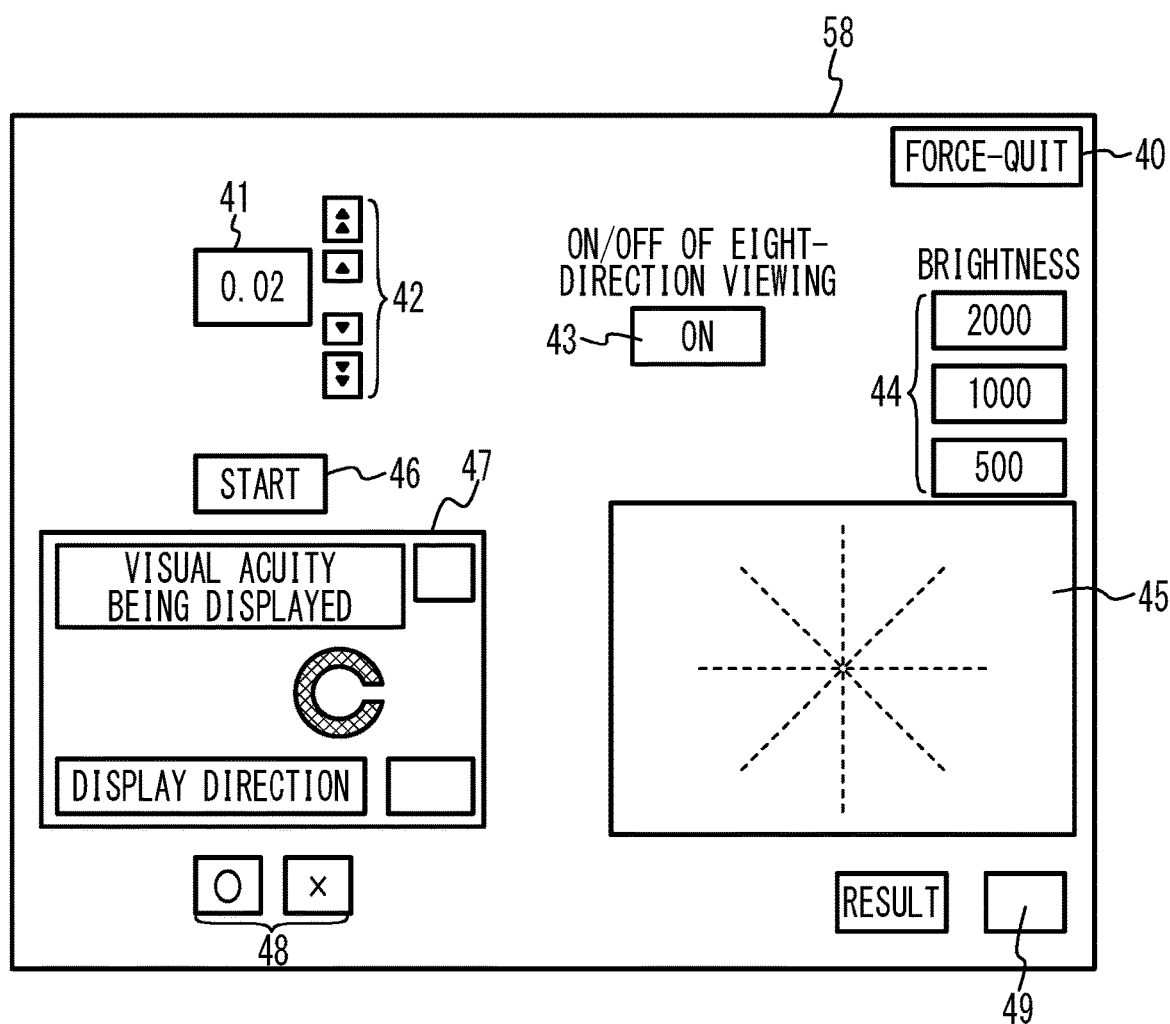
FIG. 15 illustrates an example of a screen of a display device in the first embodiment.

FIG. 15 illustrates an example of a screen of the display device in the first embodiment. The display device includes the input unit 22 and the display unit 24 in FIG. 1, and a screen 58 of the display device is a touch panel. As illustrated in FIG. 15, various indications and buttons of the touch panel are displayed on the screen 58. The initial visual acuity is displayed in a display 41. The subject or the examiner operates a visual acuity setting button 42 in step S10 of FIG. 8 to set the initial visual acuity.

When the subject or the examiner presses a button 43 for ON/OFF of eight-direction viewing in step S14 of FIG. 8, the peripheral visual field measurement is selected, the test visual target 62 for peripheral visual field measurement illustrated in FIG. 10B is projected, and the same test visual target 62 is also displayed in a display area 45. In step S16 of FIG. 8, the subject or the examiner sets the brightness of the test visual target 62 by pressing a button 44. Since the peripheral visual field measurement is selected, in step S20 of FIG. 8, the subject or the examiner sets the location of the peripheral visual field. The location of the peripheral visual field is displayed in the display area 45. The process of FIG. 13 is started by the subject or the examiner pressing a button 46. A display 47 allows the examiner to check the test visual target 62 that is being displayed. In steps S44 and S54 of FIG. 13, the subject or the examiner inputs a result by pressing a button 48. In step S24 of FIG. 8, the test result is displayed in a display 49. A button 40 is a button for force-quitting the test during the test.

In the first embodiment, the projection unit 10 projects the image 60 on the retina 74 of the subject with use of the laser beam 50 by two-dimensionally scanning the laser beam 50. The beam diameter setting unit (e.g., the aperture 25) sets the beam diameter of the laser beam 50 (step S11 of FIG. 8). The numerical aperture setting unit (e.g., the collimating lens 27) sets the numerical aperture of the laser beam 50 (step S41 of FIG. 13). The projection unit 10 projects the image 60 (a test image) for measuring the visual information of the subject on the retina 74 with use of the laser beam 50 having a set beam diameter and a set numerical aperture (steps S42 and S52 of FIG. 13). Thereafter, the control unit 20 or the examiner measures the visual information of the subject in accordance with the response corresponding to the visual recognition of the image 60 by the subject. This allows the appropriate vision test of the subject to be performed by appropriately setting the beam diameter and the numerical aperture of the laser beam 50 as in the experiment 1, and the simulations 1 and 2.

As in step S32 of FIG. 11, the projection unit 10 projects the adjustment image 63 for setting the numerical aperture suitable for the subject on the retina 74 based on the change in the numerical aperture. Thereafter, the control unit 20 or the examiner determines the numerical aperture suitable for the subject based on the response of the subject input to the input unit 22 in accordance with the change in the numerical aperture. As in the experiment 1 and the simulations 1 and 2, the numerical aperture suitable for the subject can be set by setting the beam diameter of the laser beam 50 appropriately. Since the ophthalmologist or the optometrist does not need to adjust the refractive index of the lens, it becomes possible to easily set the numerical aperture suitable for the subject. The numerical aperture suitable for the subject allows the degree of hyperopia, the degree of myopia, and the focal length of the subject to be determined.

As described in FIG. 13, the numerical aperture setting unit (e.g., the collimating lens 27) sets a numerical aperture suitable for the subject (step S40). The projection unit 10 projects the image 60 (a test image) on the retina 74 with use of the laser beam 50 having the numerical aperture suitable for the subject (steps S42 and S52). As seen above, the visual information such as the maximum acquired visual acuity or the like can be measured by setting the numerical aperture at the numerical aperture suitable for the subject and measuring the visual acuity of the subject.

For example, by measuring the acquired visual acuity before cataract surgery or a corneal transplant operation due to ametropia of the cornea, it is possible to check how much the vision will be restored after the operation. In addition, measurement of the acquired visual acuity allows the diagnosis of a retina disease and the advance diagnosis of cataract.

The response corresponding to the visual recognition of the image 60 by the subject is input to the input unit 22. The control unit 20 (a testing unit) measures the visual information of the subject based on the response input to the input unit 22. This configuration allows the control unit 20 to measure the visual information.

As described in FIG. 11, the control unit 20 determines the numerical aperture suitable for the subject (step S38) based on the response of the subject input to the input unit 22 (step S36) in accordance with the change in the numerical aperture (step S34). As described in FIG. 13, the control unit 20 projects the image 60 on the retina 74 (steps S42 and S52) with use of the laser beam having the numerical aperture suitable for the subject (step S40), and measures the visual information of the subject (step S62) based on the response input to the input unit 22 in accordance with the visual recognition of the image 60 (step S54). This configuration allows the control unit 20 to measure the visual information of the subject with use of the numerical aperture suitable for the subject.

As described in FIG. 9, the image 60 contains the test visual targets 62 with different sizes for measuring the visual information of the subject. This configuration allows the visual acuity of the subject to be determined.

In steps S14 and S20 in FIG. 8, information on the location within the retina 74 on which the test visual target 62 for measuring the visual information of the subject is to be projected is input to the input unit 22. In steps S42 and S52 of FIG. 13, the projection unit 10 projects, on the retina 74, the image 60 (a test image) including the test visual target 62 in the location within the retina 74 corresponding to the information on the location. This configuration allows the control unit 20 or the examiner to conduct the central visual field measurement or the peripheral visual field measurement.

The above-described operations in the first embodiment allow the vision test based on the measurement of the visual acuity and the visual field, which are visual information, of the subject to be conducted.

[Calculation of the Diopter Value]

Figure 16A:
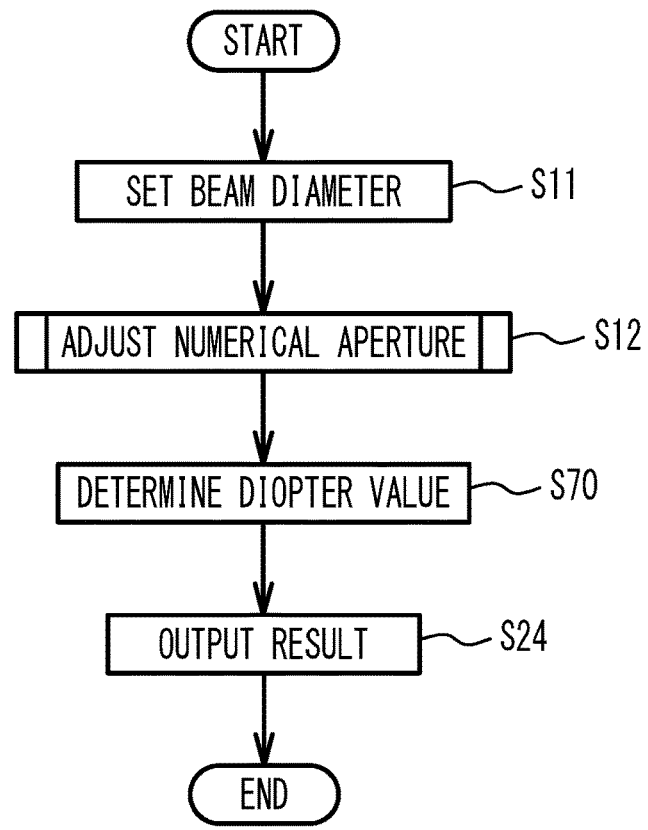
FIG. 16A is a flowchart of a process of calculating a diopter value in the first embodiment.

FIG. 16A is a flowchart of a process of calculating the diopter value in the first embodiment. As illustrated in FIG. 16A, as in step S11 of FIG. 8, the beam diameter of the laser beam 50 is set (step S11). For example, the beam diameter is set at greater than 800 µm. As in step S12 of FIG. 8, the numerical aperture is adjusted (step S12). The diopter value is determined (step S70). For example, the diopter value is determined based on the numerical aperture suitable for the subject determined in step S12. The diopter value is determined by, for example, the control unit 20 or the examiner.

Since the diopter value is calculated as the reciprocal of the focal length, a table storing the correspondence relationship between the position of the collimating lens 27 and the diopter value is stored in the storage unit 23 in advance. The control unit 20 refers to the table to obtain the diopter value based on the position of the collimating lens 27. Thereby, the diopter value can be calculated. Alternatively, a table storing the correspondence relationship between the numerical aperture suitable for the subject and the diopter value may be stored, and the diopter value corresponding to the numerical aperture suitable for the subject may be obtained in the similar manner. The calculation result of the diopter value is output (step S24).

In step S12 of FIG. 16A, the projection unit 10 projects an image for calculating the diopter value of the subject based on the change in the numerical aperture (for example, the adjustment image 63 in FIG. 12A and FIG. 12B) on the retina (step S32 in FIG. 11). Thereafter, the control unit 20 or the examiner determines the diopter value of the subject based on the numerical aperture most suitable for the subject determined in step S38 of FIG. 11 (step S70). As described above, the diopter value of the subject can be calculated by changing the numerical aperture. Since the ophthalmologist or the optometrist does not need to adjust the refractive index of the lens, it becomes possible to easily calculate the diopter value.

[Measurement of Astigmatism]

Figure 16B:
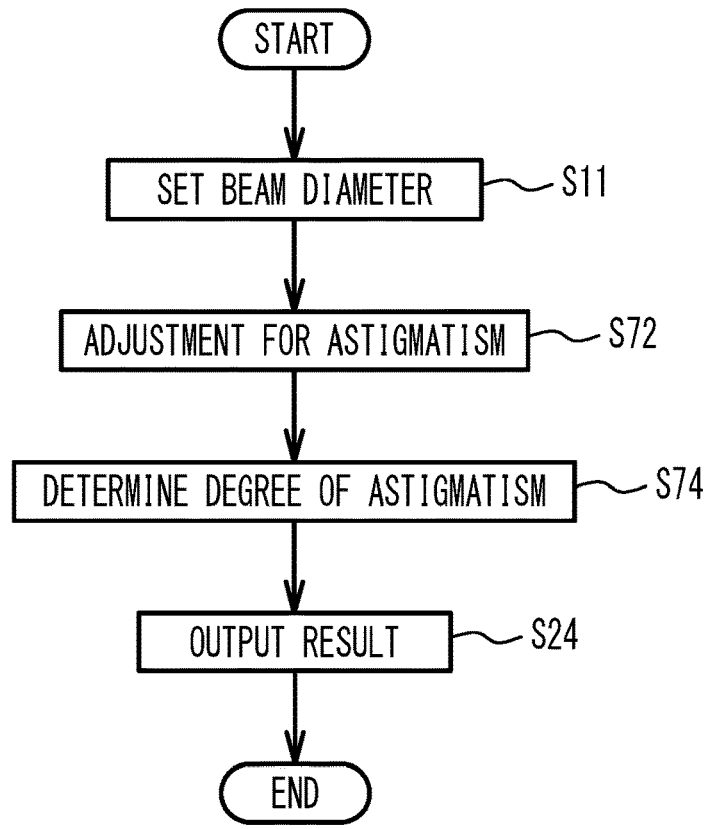
FIG. 16B is a flowchart of a process of assessing astigmatism in the first embodiment.

FIG. 16B is a flowchart of a process of assessing astigmatism in the first embodiment. As illustrated in FIG. 16B, as in step S11 of FIG. 8, the beam diameter of the laser beam 50 is set (step S11). For example, the beam diameter is set at greater than 800 µm.

Adjustment for astigmatism is performed (step S72). For example, the toric lens 26 that makes the condensing power of the laser beam different depending on the direction in the cross-section of the laser beam is arranged such that the laser beam 50 passes through the toric lens 26. The projection unit 10 projects an astigmatism test image (e.g., a checkered pattern in FIG. 12A) on the retina 74. The toric lens 26 is rotated with respect to the laser beam 50, and/or the toric lenses 26 with different curvatures are used. The toric lens 26 is adjusted such that the astigmatism test image viewed by the subject is not distorted. The astigmatic axis direction of the subject can be adjusted by rotating the toric lens 26. The diopter for the subject can be adjusted by using the toric lenses 26 with different curvatures. The control unit 20 or the examiner performs the adjustment for astigmatism.

The degree of astigmatism is determined based on the result of the adjustment for astigmatism (step S74). For example, the astigmatic axis direction and the diopter of the subject are determined based on the adjustment result of the toric lens 26. The control unit 20 or the examiner determines the degree of astigmatism. The results of the degree of astigmatism is output (step S24).

As illustrated in FIG. 16B, astigmatism of the subject can be assessed by adjusting the toric lens 26. Since the ophthalmologist or the optometrist does not need to adjust the distortion of the lens, it is possible to easily assess astigmatism.

As described above, the test image for measuring the visual information of the subject is the image for measuring the visual acuity or visual field as the visual information of the subject or the image for assessing astigmatism.

The beam diameter setting unit (e.g., the aperture 25) sets the beam diameter of the laser beam 50 at greater than 800 µm (step S11 in FIG. 8). The projection unit 10 projects the image 60 (a test image) for measuring the visual information of the subject on the retina 74 with use of the laser beam having a beam diameter greater than 800 µm (steps S42 and S52 in FIG. 13). Since the laser beam is less likely to be affected by the anterior eye part as in the experiment 1 and the simulations 1 and 2, the measurement of the visual information such as the acquired visual acuity or the like, the measurement of the visual field, setting of the numerical aperture suitable for the subject, calculation of the diopter value, and/or the assessment of astigmatism becomes possible.

[Adjustment of the Beam Diameter]

Figure 17:
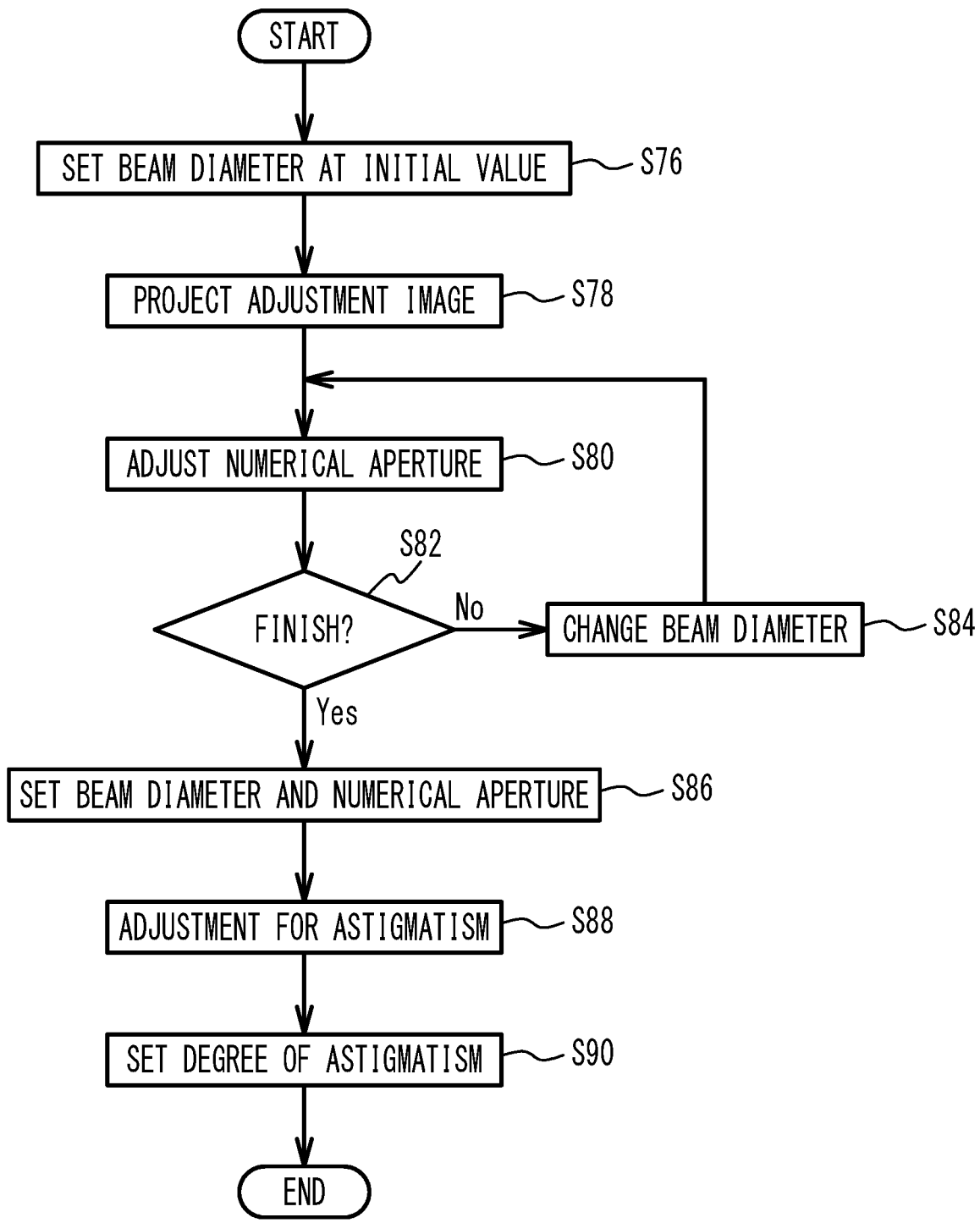
FIG. 17 is a flowchart illustrating an example of an adjustment process in the first embodiment.

In the above examples, an example in which the vision test is conducted while the beam diameter of the laser beam 50 is fixed (for example, fixed to greater than 800 µm) is described. However, the beam diameter of the laser beam 50 when entering the cornea 72 may be adjusted. FIG. 17 is a flowchart of an example of the adjustment process (step S12 of FIG. 8) in the first embodiment.

As illustrated in FIG. 17, the beam diameter is set at an initial value (step S76). The control unit 20 or the examiner sets the beam diameter as in step S11 of FIG. 8. For example, the beam diameter is set at 900 µm. The control unit 20 displays an image (step S78). For example, the projection unit 10 projects a Landolt ring or the adjustment image 63 illustrated in FIG. 12A or FIG. 12B on the retina 74 according to the instruction from the control unit 20.

As in steps S34 to S38 in FIG. 11, the numerical aperture is adjusted (step S80). It is determined whether changing of the beam diameter is finished (step S82). When the determination is No, the beam diameter is changed (step S84). For example, the beam diameter is set at 1200 μm. Thereafter, the process returns to step S80. The beam diameter is changed to up to, for example, 3000 μm at desired intervals.

For example, when the numerical aperture is adjusted with the beam diameter of 3000 μm, the determination in step S82 becomes Yes. When the determination is Yes in step S82, the beam diameter and the numerical aperture are determined (step S86). For example, the control unit 20 or the examiner respectively sets the beam diameter and the numerical aperture at the beam diameter and the numerical aperture at which the subject can visually recognize the adjustment image best (step S88). For example, the control unit 20 or the examiner conducts the adjustment for astigmatism as in step S72 of FIG. 16B. The degree of astigmatism is set (step S90). For example, the control unit 20 or the examiner sets the toric lens 26 most suitable for the subject. Thereafter, the process returns to FIG. 8.

As illustrated in FIG. 17, the visual acuity test is conducted in FIG. 8 after the beam diameter suitable for the subject, the numerical aperture suitable for the subject, and the degree of astigmatism are set. Thereby, the maximum acquired visual acuity of the subject can be measured.

First Variation of the First Embodiment

Figure 18:
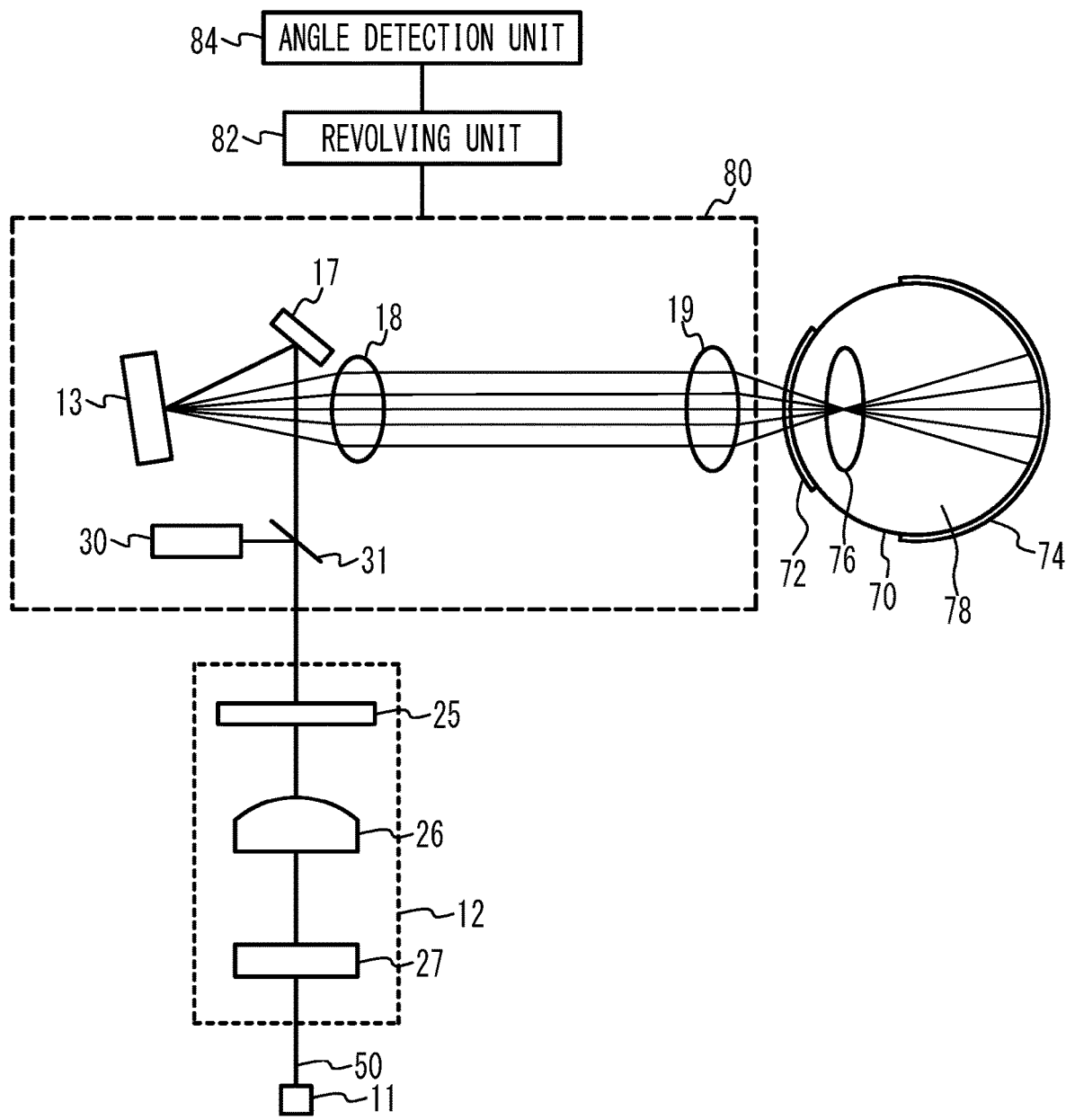
FIG. 18 illustrates an optical system of a vision test device in accordance with a first variation of the first embodiment.

A first variation of the first embodiment is an example in which a function of measuring the angle of squint is provided. FIG. 18 illustrates an optical system of a vision test device in accordance with the first variation of the first embodiment. As illustrated in FIG. 18, a projection block 80 includes the scan unit 13, a planar mirror 17, and lenses 18 and 19. A revolving unit 82 revolves the projection block 80 around the eyeball 70. The revolving unit 82 is, for example, an actuator that drives the projection block 80. An angle detection unit 84 detects the angle of the projection block 80 to the eyeball 70. The revolving unit 82 may revolve the whole projection unit 10 or revolve a part of the projection unit 10 as long as the direction in which the laser beam 50 is emitted to the eyeball 70 can be changed. Other structures are the same as those of the first embodiment, and the description thereof is thus omitted.

Figure 19A:
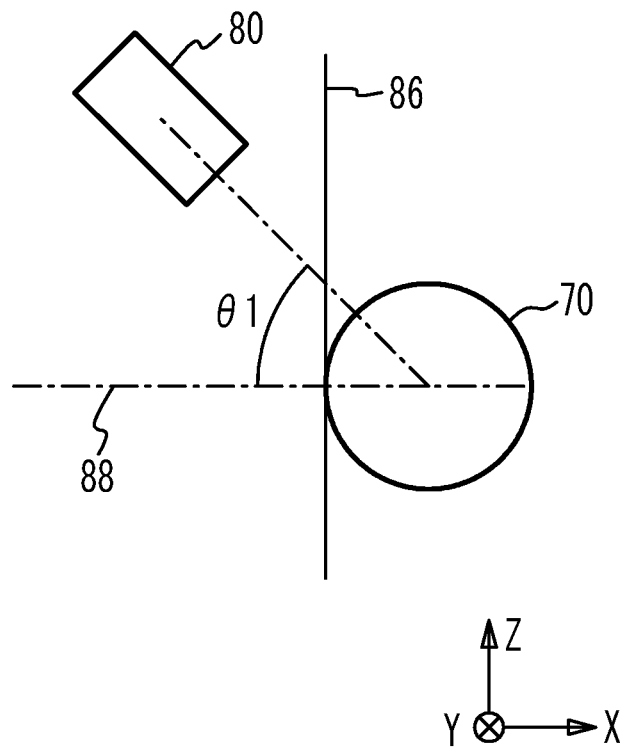
FIG. 19A and FIG. 19B illustrate an angle of a revolving unit in the first variation of the first embodiment.
Figure 19B:
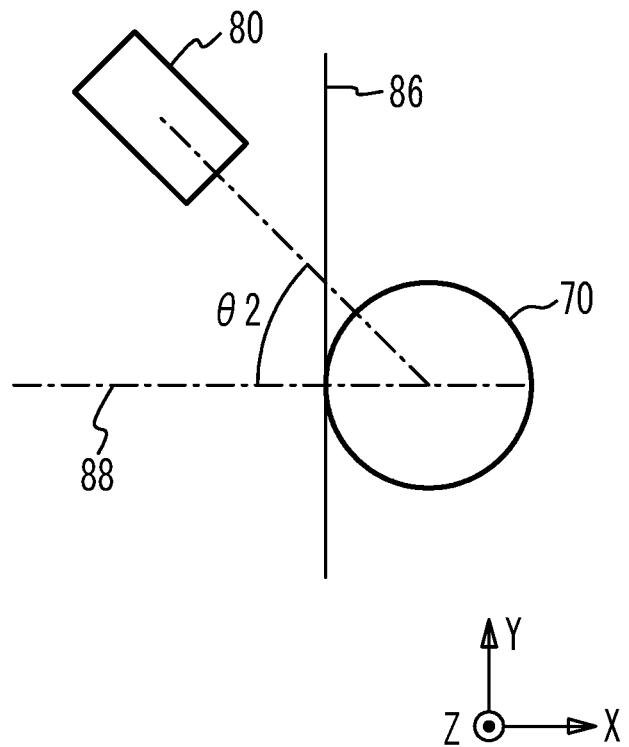

FIG. 19A and FIG. 19B illustrate the angle of the revolving unit in the first variation of the first embodiment. The YZ plane is the front face of a face 86 of the subject. The positive Z direction is the upward direction of the face 86, the negative Z direction is the downward direction of the face 86, the positive Y direction is the rightward direction as viewed from the subject, the negative Y direction is the leftward direction as viewed from the subject, and the negative X direction is the normal direction to the face 86.

As illustrated in FIG. 19A, the angle in the Z direction of the projection block 80 to a normal line 88 of the face 86 is defined as an angle θ1. As illustrated in FIG. 19B, the angle in the Y direction of the projection block 80 to the normal line 88 of the face 86 is defined as an angle θ2. The angles θ1 and θ2 are angles of the projection block 80 to the eyeball 70.

Figure 20:
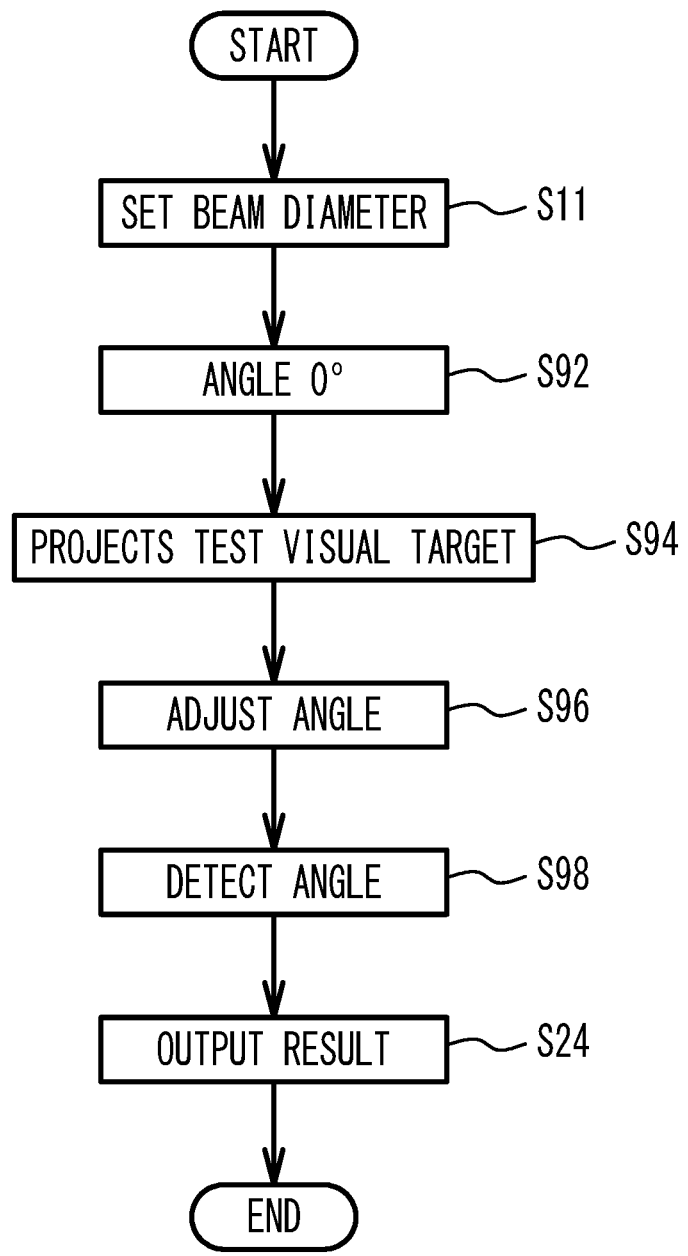
FIG. 20 is a flowchart of a process of measuring an angle of squint in the first variation of the first embodiment.

FIG. 20 is a flowchart of a process of measuring the angle of squint in the first variation of the first embodiment. As illustrated in FIG. 20, as in step S11 of FIG. 8, the beam diameter of the laser beam 50 is set (step S11). For example, the beam diameter is set at greater than 800 μm. The control unit 20 or the examiner sets the angles θ1 and θ2 at 0° in a state where the subject faces front (step S92). The control unit 20 or the examiner projects the test visual target on the retina 74 (step S94). The test visual target is, for example, the test visual target 62 in FIG. 10A.

In the case where the subject does not have a squint, when the angles θ1 and θ2 are set at 0°, the subject facing front can see the test visual target, which is located in the center of the image, in the center of the visual field. In the case where the subject has a squint, even when the subject intends to face front, the pupil does not face the front (the negative X direction). Thus, even when the angles θ1 and θ2 are set at 0°, the test visual target, which is located in the center of the image, is not projected on the center of the retina 74. Thus, the subject cannot visually recognize the test visual target in the center of the visual field. Thus, the subject adjusts the angles θ1 and θ2 (step S96). For example, the subject revolves the projection block 80 with use of the revolving unit 82. When the subject visually recognizes the test visual target in the center of the visual field, the control unit 20 or the examiner causes the angle detection unit 84 to detect the angles θ1 and θ2 (step S98). The control unit 20 outputs the angles θ1 and θ2 detected by the angle detection unit 84 as information relating to the angle of squint of the subject (step S24).

In the first variation of the first embodiment, the revolving unit 82 revolves the laser beam 50 to be emitted to the eyeball 70 of the subject with respect to the eyeball 70. The angle detection unit 84 detects the angles θ1 and θ2 of the laser beam 50 emitted to the eyeball 70 to the eyeball 70. This configuration allows the angle of squint of the subject to be examined.

Although embodiments of the present invention have been specifically described, the present invention is not limited to those particular embodiments, and various changes and modifications may be made to them without departing from the scope of the invention disclosed in the claims.

DESCRIPTION OF NUMERAL REFERENCES 10 projection unit
11 light source
13 scan unit
20 control unit
22 input unit
24 display unit
25 aperture
26 toric lens
27 collimating lens
60 image
62 test visual target
70 eyeball
72 cornea
74 retina
76 crystalline lens
78 vitreous body
80 projection block
82 revolving unit
84 angle detection unit

The invention claimed is:
1. A vision test device comprising:
   a projection unit that projects a test image on a retina of a subject with use of a laser beam by two-dimensionally scanning the laser beam, further including;
   a beam diameter setting unit that sets a beam diameter of the laser beam to a set beam diameter; and
   a numerical aperture setting unit that sets a numerical aperture of the laser beam to a set numerical aperture;

an input unit receiving a response corresponding to visual recognition of the test image from the subject to generate a response input; and a control unit connected to the input unit, the beam diameter setting unit and the numerical aperture setting unit that measures visual information of the subject based on the response input from the input unit, wherein the projection unit projects, on the retina, the test image for measuring the visual information of the subject with use of the laser beam having the set beam diameter and the set numerical aperture, and the control unit determines a value for the set numerical aperture for obtaining maximum acquired visual acuity for the subject based on the response input of the subject from the input unit in accordance with a change in the set numerical aperture, and measures the visual information of the subject based on the response input to the input unit in accordance with the visual recognition of the test image projected on the retina with use of the laser beam having the set numerical aperture for obtaining maximum acquired visual acuity for the subject.

2. The vision test device according to claim 1, wherein the numerical aperture setting unit sets the numerical aperture of the laser beam at the set numerical aperture for the subject, and the projection unit projects, on the retina, the test image for measuring the visual information of the subject with use of the laser beam having the set numerical aperture for the subject.

3. The vision test device according to claim 1, wherein the test image is an image for measuring visual acuity or a visual field as the visual information of the subject or an image for assessing astigmatism.

4. The vision test device according to claim 1, wherein the test image contains test visual targets having different sizes for measuring the visual information of the subject.

5. The vision test device according to claim 1, wherein the test image includes a fixation target for fixing a line of sight of the subject and a test visual target for measuring the visual information.

6. The vision test device according to claim 1, wherein the test image includes a test visual target for measuring the visual information, and the test visual target blinks.

7. The vision test device according to claim 1, wherein the input unit to which information on a location within the retina on which a test visual target is for measuring the visual information of the subject is to be projected, wherein the projection unit projects the test image on the retina such that the test visual target is projected on a location within the retina corresponding to the information on the location.

8. The vision test device according to claim 1, wherein the beam diameter setting unit sets the set beam diameter of the laser beam at greater than 800 μm, and the projection unit projects, on the retina, the test image for measuring the visual information of the subject with use of the laser beam with the set beam diameter greater than 800 μm.

9. The vision test device according to claim 1, further comprising:

a revolving unit structurally connected to at least a part of the projection unit for revolving the laser beam emitted to an eyeball of the subject with respect to the eyeball; and an angle detection unit connected to the revolving unit for detecting an angle of the laser beam emitted to the eyeball.

* * * * *